(12) United States Patent
Hu et al.

(10) Patent No.: US 6,368,824 B1
(45) Date of Patent: *Apr. 9, 2002

(54) NEUROPEPTIDE Y RECEPTOR Y5 AND NUCLEIC ACID SEQUENCES

(75) Inventors: Yinghe Hu, North Haven; Michael L. McCaleb, Madison; Brian T. Bloomquist, New Haven; Jaime R. Flores-Riveros, Madison; Linda J. Cornfield, Hamden, all of CT (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,035

(22) Filed: Jun. 7, 1999

Related U.S. Application Data

(63) Continuation of application No. 08/838,399, filed on Apr. 7, 1997, now Pat. No. 5,965,392.
(60) Provisional application No. 60/014,969, filed on Apr. 8, 1996.

(51) Int. Cl.⁷ .............................. C12P 21/06; C12N 5/00; C12N 15/00; C07H 21/02; C07H 21/04
(52) U.S. Cl. ................... 435/69.1; 435/320.1; 435/325; 435/455; 536/23.1; 536/23.5; 536/24.31
(58) Field of Search .............................. 435/69.1, 320.1, 435/325, 455, 366; 536/23.1, 23.5, 24.31

(56) References Cited

U.S. PATENT DOCUMENTS

| | | |
|---|---|---|
| 4,683,195 A | 7/1987 | Mullis et al. .................. 435/6 |
| 4,683,202 A | 7/1987 | Mullis et al. .................. 435/91 |
| 4,736,866 A | 4/1988 | Leder et al. .................... 800/1 |
| 5,175,383 A | 12/1992 | Leder et al. .................... 800/1 |
| 5,602,024 A * | 2/1997 | Gerald et al. ............... 435/325 |
| 5,965,392 A * | 10/1999 | Hu et al. .................... 435/69.1 |

FOREIGN PATENT DOCUMENTS

| | | |
|---|---|---|
| WO | WO 93/09227 | 5/1993 |
| WO | WO 93/12139 | 6/1993 |
| WO | WO 93/24515 | 12/1993 |
| WO | WO 95/17906 | 4/1995 |
| WO | WO 95/21245 | 8/1995 |
| WO | WO 96/14331 | 5/1996 |
| WO | WO 96/16542 | 6/1996 |
| WO | WO 97/17440 | 5/1997 |
| WO | WO 97/20821 | 6/1997 |

OTHER PUBLICATIONS

O'Shea et al., (Jan. 1997), "Neuropeptide Y Induced Feeding In The Rat Is Mediated By A Novel Receptor." *Endocrinology*, vol. 138, No. 1, pp. 196–202.
Weinberg et al., (Jul. 1996), "Cloning And Expression Of A Novel Neuropeptide Y Receptor." *Jrnl. Biol. Chem.*, vol. 271, No. 28, pp. 16435–16438.
Rose et al., (Feb. 1997), "Molecular Genetic Analysis Of A Human Neuropeptide Y Receptor." *Jrnl. Biol. Chem.*, vol. 272, No. 6, pp. 3622–3627.
Herzog et al., (May 1997), "Overlapping Gene Structure Of The Human Neuropeptide Y Receptor Subtypes Y1 And Y5 Suggest Coordinate Transcription Regulation." *Genomics*, vol. 41, No. 3, pp. 315–319.
Thomas &Capecchi, (1987) "Site–Directed Mutagenesis by Gene Targeting in Mouse Embryo–Derived Stem Cells.", *Cell*, vol. 51, pp. 503–512.
Tissue Culture (1973) Academic Press, Kruse & Patterson.
Zimmer and Gruss, (1989) "Production of chimaeric mice containing embryonic stem (ES) cells carrying a homoeobox Hox 1.1 allele mutated by homologous recombination." *Nature*, vol. 338, p. 150.
Bertling, (1987) *Bioscience Reports*, vol. 7, pp. 107–112.
Bottcher et al., (1984) *Regul. Pept.*, vol. 8, pp. 261.
Capecchi et al., (1989), *Science*, vol. 244, pp. 1288.
Colmers et al., (1993) The Biology of Neuropeptide Y and Related Peptides (Humana Press, Totowa, NJ.).
Dumont et al., (1993) *The Journal of Neuroscience*, vol. 13, No. 1, pp. 73–86.
Eva et al., (1992) *FEBS Lett.*, vol. 314, p. 285.
Gerald et al., (1996) *Nature*, vol. 382, p. 168.
Glover, (1985) *J. Biochem.*, vol. 142, p. 379.
Gordon et al., (1990) *J. Neurochem*, vol. 55, p. 506.
Gubler et al., (1983) *Gene*, vol. 25, p. 263.
Hanks et al., (1995) *Science*, vol. 269, p. 679.
Hasty et al., (1991) *Nature*, vol. 350, p. 243.
Hazlewood, (1993) *Proc. Soc. Exp. Biol. Med.*, vol. 202, p. 44.
Herzog, (1997) *Genomics*, vol. 41, p. 315–319.
Hogan et al., (1986) Manipulating the Mouse Embryo, A Laboratory Manual.
Howlett, (1996) *Nature*, vol. 382, p. 113.
Hu et al., (1996) *The Journal of Biological Chemistry*, vol. 271, No. 42, p. 26315–26319.
Invitrogen Corporation publications 130813sa and 130928sa.
Kalra et al., (1991) *Phys. & Behavior*, vol. 50, p. 5.
Katuski et al., (1988) *Science*, vol. 241, p. 593.

(List continued on next page.)

*Primary Examiner*—Scott D. Priebe
*Assistant Examiner*—Sumesh Kaushal
(74) *Attorney, Agent, or Firm*—McDonnell Boehnen Hulbert & Berghoff

(57) ABSTRACT

The present invention provides novel NPY/PYY receptor proteins and the nucleic acid sequence encoding them. The invention is directed to the isolation, characterization, and pharmacological use of these receptors and nucleic acids. In particular, this invention provides human and rat NPY/PYY receptors (which we call the NPY Y5 receptor) and nucleic acids. Also provided are recombinant expression constructs useful for transfecting cells and expressing the protein in vitro and in vivo. The invention further provides methods for detecting expression levels of the protein as well as methods for screening for receptor antagonists and agonists to be used for the treatment of obesity or anorexia, respectively.

15 Claims, 2 Drawing Sheets

OTHER PUBLICATIONS

Kuhn et al., (1995) *Science*, vol. 269, p. 1427.
Larhammar et al., (1992) *J. Biol. Chem.* vol. 267, p. 10935.
Lundell et al., (1995) *J. Biol. Chem.*, vol. 270, p. 29123.
Marx, (1995) *Science*, vol. 269, p. 636.
Maxam et al., (1980), *Methods in Enzymology*, vol. 65, pp. 499–650.
Morley et al., (1985) *Brain Res.,* , vol. 341, p. 200.
Nakamura et al., (1995) *J. Biol. Chem.*, vol. 270, p. 30102.
Okayama et al., (1982) *Molec. Cell. Biol.*, vol. 2, p. 161.
Rose et al., (1995) *J. Biol. Chem.* vol. 270, p. 22661.
Sambrook et al., (1989) Molecular Cloning: A Laboratory Manual, ($2^{nd}$ Edition, Cold Spring Harbor Press, New York).
Smithies et al., (1985) *Nature*, vol. 317, pp. 231–234.
Stacey et al., (1994) *Mol. Cell. Biol.*, vol. 31, pp. 581–587.
Tatemoto et al., (1982) *Nature*, vol. 296, p. 659.
Tatemoto, (1982) *Proc. Natl. Acad. Sci.*, vol. 79, p. 5485.
Gehlert, Donald R., (1994), "Subtypes of Receptors For Neuropeptide Y: Implications For the Targeting of Therapeutics.", *Life Sciences*, vol. 55, No. 8, pp. 551–562.

Whalestedt, (1993), Neuropeptide Y–related Peptides And Their Receptors–Are The Receptors Potential Therapeutic Drug Targets. *Annual Review of Pharmacology And Toxicology*, vol. 32, pp. 309–352.

Tatemoto et al., (Feb. 1992), "Synthesis of Receptor Antagonist of Neuropeptide Y." *Proc. Natl. Acad. Sci.*, vol. 89, No. 4, pp. 1174–1178.

Hu et al., (Oct. 1996), "Identification of a Novel Hypothalamic Neuropeptide Y Receptor Associated With Feeding Behavior." *Journal of Biological Chemistry*, vol. 271, No. 42.

Gerald et al., (Jul. 1996), "A Receptor Subtype Involved In Neuropeptide–Y–Induced Food Intake." vol. 382, No. 6587, pp. 168–171.

* cited by examiner

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 2481 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 248..1585

(ix) FEATURE:
      (A) NAME/KEY: mat_peptide
      (B) LOCATION: 248..1582

(xi) SEQUENCE DESCRIPTION: SEQ ID NO: 1:

```
GAATTCTTGG ACTATGGGGG CCGGGAACAG GCGATCTTGA GCCGGGTGTC CGGGGTCTCA        60

GGGACTGTCA CGTGTTCCCG AGGTGCTTCT AAAACCCTGG CGGCTCCGGA GCCCCTCCTT       120

CCCACCACCG CCTCCAGGTC CTGCTCCTGC CGCCACCGCT TCCATCTGGA GCAGAAGCGA       180

CCGCGCTCAG CCACGTACCC CGGAGTCCAG GCACCCGCAG CGGCCGGGGC ATCCCGAGGA       240

TTTTAGT ATG GAG TTT AAG CTT GAG GAG CAT TTT AAC AAG ACA TTT GTC        289
        Met Glu Phe Lys Leu Glu Glu His Phe Asn Lys Thr Phe Val
         1               5                  10

ACA GAG AAC AAT ACA GCT GCT GCT CGG AAT GCA GCC TTC CCT GCC TGG        337
Thr Glu Asn Asn Thr Ala Ala Ala Arg Asn Ala Ala Phe Pro Ala Trp
 15                  20                  25                  30

GAG GAC TAC AGA GGC AGC GTA GAC GAT TTA CAA TAC TTT CTG ATT GGG        385
Glu Asp Tyr Arg Gly Ser Val Asp Asp Leu Gln Tyr Phe Leu Ile Gly
                 35                  40                  45

CTC TAT ACA TTC GTA AGT CTT CTT GGC TTT ATG GGC AAT CTA CCT ATT        433
Leu Tyr Thr Phe Val Ser Leu Leu Gly Phe Met Gly Asn Leu Pro Ile
                 50                  55                  60

TTA ATG GCT GTT ATG AAA AAG CGC AAT CAG AAG ACT ACA GTG AAC TTT        481
Leu Met Ala Val Met Lys Lys Arg Asn Gln Lys Thr Thr Val Asn Phe
             65                  70                  75

CTC ATA GGC AAC CTG GCC TTC TCC GAC ATC TTG GTC GTC CTG TTT TGC        529
Leu Ile Gly Asn Leu Ala Phe Ser Asp Ile Leu Val Val Leu Phe Cys
         80                  85                  90

TCC CCT TTC ACC CTG ACC TCT GTC TTG TTG GAT CAG TGG ATG TTT GGC        577
Ser Pro Phe Thr Leu Thr Ser Val Leu Leu Asp Gln Trp Met Phe Gly
 95                 100                 105                 110

AAA GCC ATG TGC CAT ATC ATG CCG TTC CTT CAA TGT GTG TCA GTT CTG        625
Lys Ala Met Cys His Ile Met Pro Phe Leu Gln Cys Val Ser Val Leu
                115                 120                 125

GTT TCA ACT CTG ATT TTA ATA TCA ATT GCC ATT GTC AGG TAT CAT ATG        673
Val Ser Thr Leu Ile Leu Ile Ser Ile Ala Ile Val Arg Tyr His Met
                130                 135                 140

ATA AAG CAC CCT ATT TCT AAC AAT TTA ACG GCA AAC CAT GGC TAC TTC        721
Ile Lys His Pro Ile Ser Asn Asn Leu Thr Ala Asn His Gly Tyr Phe
            145                 150                 155
```

```
CTG ATA GCT ACT GTC TGG ACA CTG GGC TTT GCC ATC TGT TCT CCC CTC        769
Leu Ile Ala Thr Val Trp Thr Leu Gly Phe Ala Ile Cys Ser Pro Leu
    160                 165                 170

CCA GTG TTT CAC AGT CTT GTG GAA CTT AAG GAG ACC TTT GGC TCA GCA        817
Pro Val Phe His Ser Leu Val Glu Leu Lys Glu Thr Phe Gly Ser Ala
175                 180                 185                 190

CTG CTG AGT AGC AAA TAT CTC TGT GTT GAG TCA TGG CCC TCT GAT TCA        865
Leu Leu Ser Ser Lys Tyr Leu Cys Val Glu Ser Trp Pro Ser Asp Ser
                195                 200                 205

TAC AGA ATT GCT TTC ACA ATC TCT TTA TTG CTA GTG CAG TAT ATC CTG        913
Tyr Arg Ile Ala Phe Thr Ile Ser Leu Leu Leu Val Gln Tyr Ile Leu
            210                 215                 220

CCT CTA GTA TGT TTA ACG GTA AGT CAT ACC AGC GTC TGC CGA AGC ATA        961
Pro Leu Val Cys Leu Thr Val Ser His Thr Ser Val Cys Arg Ser Ile
                225                 230                 235

AGC TGT GGA TTG TCC CAC AAA GAA AAC AGA CTC GAA GAA AAT GAG ATG       1009
Ser Cys Gly Leu Ser His Lys Glu Asn Arg Leu Glu Glu Asn Glu Met
240                 245                 250

ATC AAC TTA ACC CTA CAG CCA TCC AAA AAG AGC AGG AAC CAG GCA AAA       1057
Ile Asn Leu Thr Leu Gln Pro Ser Lys Lys Ser Arg Asn Gln Ala Lys
255                 260                 265                 270

ACC CCC AGC ACT CAA AAG TGG AGC TAC TCA TTC ATC AGA AAG CAC AGA       1105
Thr Pro Ser Thr Gln Lys Trp Ser Tyr Ser Phe Ile Arg Lys His Arg
                275                 280                 285

AGG AGG TAC AGC AAG AAG ACG GCC TGT GTC TTA CCC GCC CCA GCA GGA       1153
Arg Arg Tyr Ser Lys Lys Thr Ala Cys Val Leu Pro Ala Pro Ala Gly
            290                 295                 300

CCT TCC CAG GGG AAG CAC CTA GCC GTT CCA GAA AAT CCA GCC TCC GTC       1201
Pro Ser Gln Gly Lys His Leu Ala Val Pro Glu Asn Pro Ala Ser Val
                305                 310                 315

CGT AGC CAG CTG TCG CCA TCC AGT AAG GTC ATT CCA GGG GTC CCA ATC       1249
Arg Ser Gln Leu Ser Pro Ser Ser Lys Val Ile Pro Gly Val Pro Ile
320                 325                 330

TGC TTT GAG GTG AAA CCT GAA GAA AGC TCA GAT GCT CAT GAG ATG AGA       1297
Cys Phe Glu Val Lys Pro Glu Glu Ser Ser Asp Ala His Glu Met Arg
335                 340                 345                 350

GTC AAG CGT TCC ATC ACT AGA ATA AAA AAG AGA TCT CGA AGT GTT TTC       1345
Val Lys Arg Ser Ile Thr Arg Ile Lys Lys Arg Ser Arg Ser Val Phe
                355                 360                 365

TAC AGA CTG ACC ATA CTG ATA CTC GTG TTC GCC GTT AGC TGG ATG CCA       1393
Tyr Arg Leu Thr Ile Leu Ile Leu Val Phe Ala Val Ser Trp Met Pro
            370                 375                 380

CTC CAC GTC TTC CAC GTG GTG ACT GAC TTC AAT GAT AAC TTG ATT TCC       1441
Leu His Val Phe His Val Val Thr Asp Phe Asn Asp Asn Leu Ile Ser
                385                 390                 395

AAT AGG CAT TTC AAG CTG GTA TAC TGC ATC TGT CAC TTG TTA GGC ATG       1489
Asn Arg His Phe Lys Leu Val Tyr Cys Ile Cys His Leu Leu Gly Met
                400                 405                 410

ATG TCC TGT TGT CTA AAT CCG ATC CTA TAT GGT TTC CTT AAT AAT GGT       1537
Met Ser Cys Cys Leu Asn Pro Ile Leu Tyr Gly Phe Leu Asn Asn Gly
415                 420                 425                 430

ATC AAA GCA GAC TTG AGA GCC CTT ATC CAC TGC CTA CAC ATG TCA TGA       1585
Ile Lys Ala Asp Leu Arg Ala Leu Ile His Cys Leu His Met Ser  *
                435                 440                 445

TTCTCTCTGT GCACCAAAGA GAGAAGAAAC GTGGTAATTG ACACATAATT TATACAGAAG    1645

TATTCTGGAT CTGAATGCCA GTTCGTAATC TACGTAAGAT CATCTTCATG TTATAATATG    1705

GTTAATTCAA TCAGTTGTGC AGAGTCAATG TCCATCTAAT ACAATTTCAT GTGTTGAAGT    1765
```

-continued

```
AGTTTACATT ATTTTCCATT TTATGTCATT GGTAATAAGT TGAGTGATAC TCTGTGGTTT   1825

AGTGTAAAAG ATATAGCTAT CCAAATTGTT ACGTTGTACA AAAATGTAT GAAGTGACAA    1885

GTTGTCCCAA AGAGCATTTA ACTACAGATT TAAGGAATTT CTATTATCTG GGTATCTTCA   1945

TTTCTATTTC ACAGGCTTCT TAACATTTTT TTGTAAAAGT ACAAAAATAT TCAAAAGTCA   2005

GAACTCTATT ACAGATGTAT GCATAAAAGA TGATTATAAT TTTGTAGGAG AAAGATCTGC   2065

TCCTATTAGT GAAGATTGGT AAAATTGTCA GTTTAACCCG GCTGTCCTAC TACTAATATT   2125

TAATTTTTCA AATATGAAAA GGTTTCAGAT TTTGTTTAGA TTTATATCAC ATTAAACACT   2185

GTCAAATAAA GGCTGTTTTT ATATGCATCG TTGATGTTCC AAAATGTGAA GTCTAAATGG   2245

TGTCTGTATT TCCAATTATT AAATAACTTC TAAGATCATT TTTAAAAGTC TGTAGATGGT   2305

ATGGATAGCT AGTTGTTTGT TAATATAAAG TAAAAGTAGA TAGCTGATTT ATGTTGTACC   2365

TATGTCGTAT GTATATTAGG TATCGTGTTG TCTCACTAAA GTGAAAGCAA ACGAAAAAAA   2425

AAAAAAAAAA AAAAAAAAAA AAAAAAAAAA AAAAAAAAAA AAAAAAAAAA AAAAA        2481
```

(2) INFORMATION FOR SEQ ID NO: 2:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Phe Lys Leu Glu Glu His Phe Asn Lys Thr Phe Val Thr Glu
 1               5                  10                  15

Asn Asn Thr Ala Ala Arg Asn Ala Ala Phe Pro Ala Trp Glu Asp
            20                  25                  30

Tyr Arg Gly Ser Val Asp Asp Leu Gln Tyr Phe Leu Ile Gly Leu Tyr
        35                  40                  45

Thr Phe Val Ser Leu Leu Gly Phe Met Gly Asn Leu Pro Ile Leu Met
    50                  55                  60

Ala Val Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Ala
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Lys Glu Thr Phe Gly Ser Ala Leu Leu
            180                 185                 190

Ser Ser Lys Tyr Leu Cys Val Glu Ser Trp Pro Ser Asp Ser Tyr Arg
        195                 200                 205

Ile Ala Phe Thr Ile Ser Leu Leu Leu Val Gln Tyr Ile Leu Pro Leu
    210                 215                 220

Val Cys Leu Thr Val Ser His Thr Ser Val Cys Arg Ser Ile Ser Cys
```

```
225                 230                 235                 240
Gly Leu Ser His Lys Glu Asn Arg Leu Glu Glu Asn Glu Met Ile Asn
                245                 250                 255
Leu Thr Leu Gln Pro Ser Lys Lys Ser Arg Asn Gln Ala Lys Thr Pro
                260                 265                 270
Ser Thr Gln Lys Trp Ser Tyr Ser Phe Ile Arg Lys His Arg Arg Arg
                275                 280                 285
Tyr Ser Lys Lys Thr Ala Cys Val Leu Pro Ala Pro Ala Gly Pro Ser
            290                 295                 300
Gln Gly Lys His Leu Ala Val Pro Glu Asn Pro Ala Ser Val Arg Ser
305                 310                 315                 320
Gln Leu Ser Pro Ser Lys Val Ile Pro Gly Val Pro Ile Cys Phe
                325                 330                 335
Glu Val Lys Pro Glu Glu Ser Ser Asp Ala His Glu Met Arg Val Lys
                340                 345                 350
Arg Ser Ile Thr Arg Ile Lys Lys Arg Ser Arg Ser Val Phe Tyr Arg
                355                 360                 365
Leu Thr Ile Leu Ile Leu Val Phe Ala Val Ser Trp Met Pro Leu His
        370                 375                 380
Val Phe His Val Val Thr Asp Phe Asn Asp Asn Leu Ile Ser Asn Arg
385                 390                 395                 400
His Phe Lys Leu Val Tyr Cys Ile Cys His Leu Leu Gly Met Met Ser
                405                 410                 415
Cys Cys Leu Asn Pro Ile Leu Tyr Gly Phe Leu Asn Asn Gly Ile Lys
                420                 425                 430
Ala Asp Leu Arg Ala Leu Ile His Cys Leu His Met Ser
        435                 440                 445

(2) INFORMATION FOR SEQ ID NO: 3:

(i) SEQUENCE CHARACTERISTICS:
        (A) LENGTH: 2604 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 371..1708

(ix) FEATURE:
        (A) NAME/KEY: mat_peptide
        (B) LOCATION: 371..1705

(xi) SEQUENCE DESCRIPTION: SEQ ID NO: 3:

GAATTCTTGG ACTATGGGGG CCGGGAACAG GCGATCTTGA GCCGGGTGTC CGGGGTCTCA    60

GGGACTGTCA CGTGTTCCCG AGGTGCTTCT AAAACCCTGG CGGCTCCGGA GCCCCTCCTT   120

CCCACCACCG CCTCCAGGTC CTGCTCCTGC CGCCACCGCT TCCATCTGGA GCAGAAGCGA   180

CCGCGCTCAG CCACGTACCC CGGAGTCCAG GCACCCGCAG CGGCCGGGGC ATCCCGAGCT   240

GGCCATACAC CGGGAGACAG CTGTGCCCTT GGGTTTGCAA GGTGGCTTGG AAGTCAACTG   300

CCAGTAGGAA ATAGCCATCC ACACACCTGA GTTCCAAGGG GGAAGAAAGA GATTCTTATG   360

TGATTTTAGT ATG GAG TTT AAG CTT GAG GAG CAT TTT AAC AAG ACA TTT     409
```

```
                Met Glu Phe Lys Leu Glu Glu His Phe Asn Lys Thr Phe
                 1               5                   10

GTC ACA GAG AAC AAT ACA GCT GCT GCT CGG AAT GCA GCC TTC CCT GCC       457
Val Thr Glu Asn Asn Thr Ala Ala Ala Arg Asn Ala Ala Phe Pro Ala
    15              20                  25

TGG GAG GAC TAC AGA GGC AGC GTA GAC GAT TTA CAA TAC TTT CTG ATT       505
Trp Glu Asp Tyr Arg Gly Ser Val Asp Asp Leu Gln Tyr Phe Leu Ile
30              35                  40                  45

GGG CTC TAT ACA TTC GTA AGT CTT CTT GGC TTT ATG GGC AAT CTA CTT       553
Gly Leu Tyr Thr Phe Val Ser Leu Leu Gly Phe Met Gly Asn Leu Leu
                50                  55                  60

ATT TTA ATG GCT GTT ATG AAA AAG CGC AAT CAG AAG ACT ACA GTG AAC       601
Ile Leu Met Ala Val Met Lys Lys Arg Asn Gln Lys Thr Thr Val Asn
                65                  70                  75

TTT CTC ATA GGC AAC CTG GCC TTC TCC GAC ATC TTG GTC GTC CTG TTT       649
Phe Leu Ile Gly Asn Leu Ala Phe Ser Asp Ile Leu Val Val Leu Phe
            80                  85                  90

TGC TCC CCT TTC ACC CTG ACC TCT GTC TTG TTG GAT CAG TGG ATG TTT       697
Cys Ser Pro Phe Thr Leu Thr Ser Val Leu Leu Asp Gln Trp Met Phe
        95                  100                 105

GGC AAA GCC ATG TGC CAT ATC ATG CCG TTC CTT CAA TGT GTG TCA GTT       745
Gly Lys Ala Met Cys His Ile Met Pro Phe Leu Gln Cys Val Ser Val
110             115                 120                 125

CTG GTT TCA ACT CTG ATT TTA ATA TCA ATT GCC ATT GTC AGG TAT CAT       793
Leu Val Ser Thr Leu Ile Leu Ile Ser Ile Ala Ile Val Arg Tyr His
                130                 135                 140

ATG ATA AAG CAC CCT ATT TCT AAC AAT TTA ACG GCA AAC CAT GGC TAC       841
Met Ile Lys His Pro Ile Ser Asn Asn Leu Thr Ala Asn His Gly Tyr
                145                 150                 155

TTC CTG ATA GCT ACT GTC TGG ACA CTG GGC TTT GCC ATC TGT TCT CCC       889
Phe Leu Ile Ala Thr Val Trp Thr Leu Gly Phe Ala Ile Cys Ser Pro
            160                 165                 170

CTC CCA GTG TTT CAC AGT CTT GTG GAA CTT AAG GAG ACC TTT GGC TCA       937
Leu Pro Val Phe His Ser Leu Val Glu Leu Lys Glu Thr Phe Gly Ser
        175                 180                 185

GCA CTG CTG AGT AGC AAA TAT CTC TGT GTT GAG TCA TGG CCC TCT GAT       985
Ala Leu Leu Ser Ser Lys Tyr Leu Cys Val Glu Ser Trp Pro Ser Asp
190             195                 200                 205

TCA TAC AGA ATT GCT TTC ACA ATC TCT TTA TTG CTA GTG CAG TAT ATC      1033
Ser Tyr Arg Ile Ala Phe Thr Ile Ser Leu Leu Val Gln Tyr Ile
                210                 215                 220

CTG CCT CTA GTA TGT TTA ACG GTA AGT CAT ACC AGC GTC TGC CGA AGC      1081
Leu Pro Leu Val Cys Leu Thr Val Ser His Thr Ser Val Cys Arg Ser
                225                 230                 235

ATA AGC TGT GGA TTG TCC CAC AAA GAA AAC AGA CTC GAA GAA AAT GAG      1129
Ile Ser Cys Gly Leu Ser His Lys Glu Asn Arg Leu Glu Glu Asn Glu
                240                 245                 250

ATG ATC AAC TTA ACC CTA CAG CCA TCC AAA AAG AGC AGG AAC CAG GCA      1177
Met Ile Asn Leu Thr Leu Gln Pro Ser Lys Lys Ser Arg Asn Gln Ala
255                 260                 265

AAA ACC CCC AGC ACT CAA AAG TGG AGC TAC TCA TTC ATC AGA AAG CAC      1225
Lys Thr Pro Ser Thr Gln Lys Trp Ser Tyr Ser Phe Ile Arg Lys His
270                 275                 280                 285

AGA AGG AGG TAC AGC AAG AAG ACG GCC TGT GTC TTA CCC GCC CCA GCA      1273
Arg Arg Arg Tyr Ser Lys Lys Thr Ala Cys Val Leu Pro Ala Pro Ala
                290                 295                 300

GGA CCT TCC CAG GGG AAG CAC CTA GCC GTT CCA GAA AAT CCA GCC TCC      1321
Gly Pro Ser Gln Gly Lys His Leu Ala Val Pro Glu Asn Pro Ala Ser
                305                 310                 315
```

```
GTC CGT AGC CAG CTG TCG CCA TCC AGT AAG GTC ATT CCA GGG GTC CCA      1369
Val Arg Ser Gln Leu Ser Pro Ser Ser Lys Val Ile Pro Gly Val Pro
        320                 325                 330

ATC TGC TTT GAG GTG AAA CCT GAA GAA AGC TCA GAT GCT CAT GAG ATG      1417
Ile Cys Phe Glu Val Lys Pro Glu Glu Ser Ser Asp Ala His Glu Met
335                 340                 345

AGA GTC AAG CGT TCC ATC ACT AGA ATA AAA AAG AGA TCT CGA AGT GTT      1465
Arg Val Lys Arg Ser Ile Thr Arg Ile Lys Lys Arg Ser Arg Ser Val
350                 355                 360                 365

TTC TAC AGA CTG ACC ATA CTG ATA CTC GTG TTC GCC GTT AGC TGG ATG      1513
Phe Tyr Arg Leu Thr Ile Leu Ile Leu Val Phe Ala Val Ser Trp Met
                370                 375                 380

CCA CTC CAC GTC TTC CAC GTG GTG ACT GAC TTC AAT GAT AAC TTG ATT      1561
Pro Leu His Val Phe His Val Val Thr Asp Phe Asn Asp Asn Leu Ile
            385                 390                 395

TCC AAT AGG CAT TTC AAG CTG GTA TAC TGC ATC TGT CAC TTG TTA GGC      1609
Ser Asn Arg His Phe Lys Leu Val Tyr Cys Ile Cys His Leu Leu Gly
        400                 405                 410

ATG ATG TCC TGT TGT CTA AAT CCG ATC CTA TAT GGT TTC CTT AAT AAT      1657
Met Met Ser Cys Cys Leu Asn Pro Ile Leu Tyr Gly Phe Leu Asn Asn
    415                 420                 425

GGT ATC AAA GCA GAC TTG AGA GCC CTT ATC CAC TGC CTA CAC ATG TCA      1705
Gly Ile Lys Ala Asp Leu Arg Ala Leu Ile His Cys Leu His Met Ser
430                 435                 440                 445

TGA TTCTCTCTGT GCACCAAAGA GAGAAGAAAC GTGGTAATTG ACACATAATT           1758
 *

TATACAGAAG TATTCTGGAT CTGAATGCCA GTTCGTAATC TACGTAAGAT CATCTTCATG    1818

TTATAATATG GTTAATTCAA TCAGTTGTGC AGAGTCAATG TCCATCTAAT ACAATTTCAT    1878

GTGTTGAAGT AGTTTACATT ATTTTCCATT TTATGTCATT GGTAATAAGT TGAGTGATAC    1938

TCTGTGGTTT AGTGTAAAAG ATATAGCTAT CCAAATTGTT ACGTTGTACA AAAAATGTAT    1998

GAAGTGACAA GTTGTCCCAA AGAGCATTTA ACTACAGATT TAAGGAATTT CTATTATCTG    2058

GGTATCTTCA TTTCTATTTC ACAGGCTTCT TAACATTTTT TTGTAAAAGT ACAAAAATAT    2118

TCAAAAGTCA GAACTCTATT ACAGATGTAT GCATAAAAGA TGATTATAAT TTTGTAGGAG    2178

AAAGATCTGC TCCTATTAGT GAAGATTGGT AAAATTGTCA GTTTAACCCG GCTGTCCTAC    2238

TACTAATATT TAATTTTTCA AATATGAAAA GGTTTCAGAT TTTGTTTAGA TTTATATCAC    2298

ATTAAACACT GTCAAATAAA GGCTGTTTTT ATATGCATCG TTGATGTTCC AAAATGTGAA    2358

GTCTAAATGG TGTCTGTATT TCCAATTATT AAATAACTTC TAAGATCATT TTTAAAAGTC    2418

TGTAGATGGT ATGGATAGCT AGTTGTTTGT TAATATAAAG TAAAAGTAGA TAGCTGATTT    2478

ATGTTGTACC TATGTCGTAT GTATATTAGG TATCGTGTTG TCTCACTAAA GTGAAAGCAA    2538

ACGAAAAAAA AAAAAAAAAA AAAAAAAAAA AAAAAAAAAA AAAAAAAAAA AAAAAAAAAA    2598

AAAAAA                                                              2604

(2) INFORMATION FOR SEQ ID NO: 4:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO: 4:

Met Glu Phe Lys Leu Glu Glu His Phe Asn Lys Thr Phe Val Thr Glu
 1               5                  10                  15
```

-continued

```
Asn Asn Thr Ala Ala Ala Arg Asn Ala Ala Phe Pro Ala Trp Glu Asp
             20                  25                  30

Tyr Arg Gly Ser Val Asp Asp Leu Gln Tyr Phe Leu Ile Gly Leu Tyr
         35                  40                  45

Thr Phe Val Ser Leu Leu Gly Phe Met Gly Asn Leu Leu Ile Leu Met
     50                  55                  60

Ala Val Met Lys Lys Arg Asn Gln Lys Thr Thr Val Asn Phe Leu Ile
 65                  70                  75                  80

Gly Asn Leu Ala Phe Ser Asp Ile Leu Val Val Leu Phe Cys Ser Pro
                 85                  90                  95

Phe Thr Leu Thr Ser Val Leu Leu Asp Gln Trp Met Phe Gly Lys Ala
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Lys Glu Thr Phe Gly Ser Ala Leu Leu
            180                 185                 190

Ser Ser Lys Tyr Leu Cys Val Glu Ser Trp Pro Ser Asp Ser Tyr Arg
        195                 200                 205

Ile Ala Phe Thr Ile Ser Leu Leu Val Gln Tyr Ile Leu Pro Leu
    210                 215                 220

Val Cys Leu Thr Val Ser His Thr Ser Val Cys Arg Ser Ile Ser Cys
225                 230                 235                 240

Gly Leu Ser His Lys Glu Asn Arg Leu Glu Glu Asn Glu Met Ile Asn
                245                 250                 255

Leu Thr Leu Gln Pro Ser Lys Lys Ser Arg Asn Gln Ala Lys Thr Pro
            260                 265                 270

Ser Thr Gln Lys Trp Ser Tyr Ser Phe Ile Arg Lys His Arg Arg Arg
        275                 280                 285

Tyr Ser Lys Lys Thr Ala Cys Val Leu Pro Ala Pro Ala Gly Pro Ser
    290                 295                 300

Gln Gly Lys His Leu Ala Val Pro Glu Asn Pro Ala Ser Val Arg Ser
305                 310                 315                 320

Gln Leu Ser Pro Ser Ser Lys Val Ile Pro Gly Val Pro Ile Cys Phe
                325                 330                 335

Glu Val Lys Pro Glu Glu Ser Ser Asp Ala His Glu Met Arg Val Lys
            340                 345                 350

Arg Ser Ile Thr Arg Ile Lys Lys Arg Ser Arg Ser Val Phe Tyr Arg
        355                 360                 365

Leu Thr Ile Leu Ile Leu Val Phe Ala Val Ser Trp Met Pro Leu His
    370                 375                 380

Val Phe His Val Val Thr Asp Phe Asn Asp Asn Leu Ile Ser Asn Arg
385                 390                 395                 400

His Phe Lys Leu Val Tyr Cys Ile Cys His Leu Leu Gly Met Met Ser
                405                 410                 415

Cys Cys Leu Asn Pro Ile Leu Tyr Gly Phe Leu Asn Asn Gly Ile Lys
            420                 425                 430
```

```
Ala Asp Leu Arg Ala Leu Ile His Cys Leu His Met Ser
        435                 440                 445
```

(2) INFORMATION FOR SEQ ID NO: 5:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (ix) FEATURE:
        (A) NAME/KEY: CDS
        (B) LOCATION: 1..1338

(ix) FEATURE:
        (A) NAME/KEY: mat_peptide
        (B) LOCATION: 1..1335

(xi) SEQUENCE DESCRIPTION: SEQ ID NO: 5:

```
ATG GAT TTA GAG CTC GAC GAG TAT TAT AAC AAG ACA CTT GCC ACA GAG      48
Met Asp Leu Glu Leu Asp Glu Tyr Tyr Asn Lys Thr Leu Ala Thr Glu
 1               5                  10                  15

AAT AAT ACT GCT GCC ACT CGG AAT TCT GAT TTC CCA GTC TGG GAT GAC      96
Asn Asn Thr Ala Ala Thr Arg Asn Ser Asp Phe Pro Val Trp Asp Asp
             20                  25                  30

TAT AAA AGC AGT GTA GAT GAC TTA CAG TAT TTT CTG ATT GGG CTC TAT     144
Tyr Lys Ser Ser Val Asp Asp Leu Gln Tyr Phe Leu Ile Gly Leu Tyr
         35                  40                  45

ACA TTT GTA AGT CTT CTT GGC TTT ATG GGG AAT CTA CTT ATT TTA ATG     192
Thr Phe Val Ser Leu Leu Gly Phe Met Gly Asn Leu Leu Ile Leu Met
     50                  55                  60

GCT CTC ATG AAA AAG CGT AAT CAG AAG ACT ACG GTA AAC TTC CTC ATA     240
Ala Leu Met Lys Lys Arg Asn Gln Lys Thr Thr Val Asn Phe Leu Ile
 65                  70                  75                  80

GGC AAT CTG GCC TTT TCT GAT ATC TTG GTT GTG CTG TTT TGC TCA CCT     288
Gly Asn Leu Ala Phe Ser Asp Ile Leu Val Val Leu Phe Cys Ser Pro
                 85                  90                  95

TTC ACA CTG ACG TCT GTC TTG CTG GAT CAG TGG ATG TTT GGC AAA GTC     336
Phe Thr Leu Thr Ser Val Leu Leu Asp Gln Trp Met Phe Gly Lys Val
            100                 105                 110

ATG TGC CAT ATT ATG CCT TTT CTT CAA TGT GTG TCA GTT TTG GTT TCA     384
Met Cys His Ile Met Pro Phe Leu Gln Cys Val Ser Val Leu Val Ser
        115                 120                 125

ACT TTA ATT TTA ATA TCA ATT GCC ATT GTC AGG TAT CAT ATG ATA AAA     432
Thr Leu Ile Leu Ile Ser Ile Ala Ile Val Arg Tyr His Met Ile Lys
    130                 135                 140

CAT CCC ATA TCT AAT AAT TTA ACA GCA AAC CAT GGC TAC TTT CTG ATA     480
His Pro Ile Ser Asn Asn Leu Thr Ala Asn His Gly Tyr Phe Leu Ile
145                 150                 155                 160

GCT ACT GTC TGG ACA CTA GGT TTT GCC ATC TGT TCT CCC CTT CCA GTG     528
Ala Thr Val Trp Thr Leu Gly Phe Ala Ile Cys Ser Pro Leu Pro Val
                165                 170                 175

TTT CAC AGT CTT GTG GAA CTT CAA GAA ACA TTT GGT TCA GCA TTG CTG     576
Phe His Ser Leu Val Glu Leu Gln Glu Thr Phe Gly Ser Ala Leu Leu
            180                 185                 190

AGC AGC AGG TAT TTA TGT GTT GAG TCA TGG CCA TCT GAT TCA TAC AGA     624
Ser Ser Arg Tyr Leu Cys Val Glu Ser Trp Pro Ser Asp Ser Tyr Arg
        195                 200                 205
```

-continued

```
ATT GCC TTT ACT ATC TCT TTA TTG CTA GTT CAG TAT ATT CTG CCC TTA      672
Ile Ala Phe Thr Ile Ser Leu Leu Leu Val Gln Tyr Ile Leu Pro Leu
    210                 215                 220

GTT TGT CTT ACT GTA AGT CAT ACA AGT GTC TGC AGA AGT ATA AGC TGT      720
Val Cys Leu Thr Val Ser His Thr Ser Val Cys Arg Ser Ile Ser Cys
225                 230                 235                 240

GGA TTG TCC AAC AAA GAA AAC AGA CTT GAA GAA AAT GAG ATG ATC AAC      768
Gly Leu Ser Asn Lys Glu Asn Arg Leu Glu Glu Asn Glu Met Ile Asn
                245                 250                 255

TTA ACT CTT CAT CCA TCC AAA AAG AGT GGG CCT CAG GTG AAA CTC TCT      816
Leu Thr Leu His Pro Ser Lys Lys Ser Gly Pro Gln Val Lys Leu Ser
                260                 265                 270

GGC AGC CAT AAA TGG AGT TAT TCA TTC ATC AAA AAA CAC AGA AGA AGA      864
Gly Ser His Lys Trp Ser Tyr Ser Phe Ile Lys Lys His Arg Arg Arg
    275                 280                 285

TAT AGC AAG AAG ACA GCA TGT GTG TTA CCT GCT CCA GAA AGA CCT TCT      912
Tyr Ser Lys Lys Thr Ala Cys Val Leu Pro Ala Pro Glu Arg Pro Ser
    290                 295                 300

CAA GAG AAC CAC TCC AGA ATA CTT CCA GAA AAC TTT GGC TCT GTA AGA      960
Gln Glu Asn His Ser Arg Ile Leu Pro Glu Asn Phe Gly Ser Val Arg
305                 310                 315                 320

AGT CAG CTC TCT TCA TCC AGT AAG TTC ATA CCA GGG GTC CCC ACT TGC     1008
Ser Gln Leu Ser Ser Ser Ser Lys Phe Ile Pro Gly Val Pro Thr Cys
                325                 330                 335

TTT GAG ATA AAA CCT GAA GAA AAT TCA GAT GTT CAT GAA TTG AGA GTA     1056
Phe Glu Ile Lys Pro Glu Glu Asn Ser Asp Val His Glu Leu Arg Val
                340                 345                 350

AAA CGT TCT GTT ACA AGA ATA AAA AAG AGA TCT CGA AGT GTT TTC TAC     1104
Lys Arg Ser Val Thr Arg Ile Lys Lys Arg Ser Arg Ser Val Phe Tyr
    355                 360                 365

AGA CTG ACC ATA CTG ATA TTA GTA TTT GCT GTT AGT TGG ATG CCA CTA     1152
Arg Leu Thr Ile Leu Ile Leu Val Phe Ala Val Ser Trp Met Pro Leu
    370                 375                 380

CAC CTT TTC CAT GTG GTA ACT GAT TTT AAT GAC AAT CTT ATT TCA AAT     1200
His Leu Phe His Val Val Thr Asp Phe Asn Asp Asn Leu Ile Ser Asn
385                 390                 395                 400

AGG CAT TTC AAG TTG GTG TAT TGC ATT TGT CAT TTG TTG GGC ATG ATG     1248
Arg His Phe Lys Leu Val Tyr Cys Ile Cys His Leu Leu Gly Met Met
                405                 410                 415

TCC TGT TGT CTT AAT CCA ATT CTA TAT GGG TTT CTT AAT AAT GGG ATT     1296
Ser Cys Cys Leu Asn Pro Ile Leu Tyr Gly Phe Leu Asn Asn Gly Ile
                420                 425                 430

AAA GCT GAT TTA GTG TCC CTT ATA CAC TGT CTT CAT ATG TAA             1338
Lys Ala Asp Leu Val Ser Leu Ile His Cys Leu His Met *
                435                 440                 445
```

(2) INFORMATION FOR SEQ ID NO: 6:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asp Leu Glu Leu Asp Glu Tyr Tyr Asn Lys Thr Leu Ala Thr Glu
 1               5                  10                  15

Asn Asn Thr Ala Ala Thr Arg Asn Ser Asp Phe Pro Val Trp Asp Asp
            20                  25                  30
```

-continued

```
Tyr Lys Ser Ser Val Asp Asp Leu Gln Tyr Phe Leu Ile Gly Leu Tyr
        35                  40                  45
Thr Phe Val Ser Leu Leu Gly Phe Met Gly Asn Leu Leu Ile Leu Met
    50                  55                  60
Ala Leu Met Lys Lys Arg Asn Gln Lys Thr Thr Val Asn Phe Leu Ile
65                  70                  75                  80
Gly Asn Leu Ala Phe Ser Asp Ile Leu Val Val Leu Phe Cys Ser Pro
                85                  90                  95
Phe Thr Leu Thr Ser Val Leu Leu Asp Gln Trp Met Phe Gly Lys Val
            100                 105                 110
Met Cys His Ile Met Pro Phe Leu Gln Cys Val Ser Val Leu Val Ser
        115                 120                 125
Thr Leu Ile Leu Ile Ser Ile Ala Ile Val Arg Tyr His Met Ile Lys
    130                 135                 140
His Pro Ile Ser Asn Asn Leu Thr Ala Asn His Gly Tyr Phe Leu Ile
145                 150                 155                 160
Ala Thr Val Trp Thr Leu Gly Phe Ala Ile Cys Ser Pro Leu Pro Val
                165                 170                 175
Phe His Ser Leu Val Glu Leu Gln Glu Thr Phe Gly Ser Ala Leu Leu
            180                 185                 190
Ser Ser Arg Tyr Leu Cys Val Glu Ser Trp Pro Ser Asp Ser Tyr Arg
        195                 200                 205
Ile Ala Phe Thr Ile Ser Leu Leu Val Gln Tyr Ile Leu Pro Leu
    210                 215                 220
Val Cys Leu Thr Val Ser His Thr Ser Val Cys Arg Ser Ile Ser Cys
225                 230                 235                 240
Gly Leu Ser Asn Lys Glu Asn Arg Leu Glu Glu Asn Glu Met Ile Asn
                245                 250                 255
Leu Thr Leu His Pro Ser Lys Lys Ser Gly Pro Gln Val Lys Leu Ser
            260                 265                 270
Gly Ser His Lys Trp Ser Tyr Ser Phe Ile Lys Lys His Arg Arg Arg
        275                 280                 285
Tyr Ser Lys Lys Thr Ala Cys Val Leu Pro Ala Pro Glu Arg Pro Ser
    290                 295                 300
Gln Glu Asn His Ser Arg Ile Leu Pro Glu Asn Phe Gly Ser Val Arg
305                 310                 315                 320
Ser Gln Leu Ser Ser Ser Lys Phe Ile Pro Gly Val Pro Thr Cys
                325                 330                 335
Phe Glu Ile Lys Pro Glu Glu Asn Ser Asp Val His Glu Leu Arg Val
            340                 345                 350
Lys Arg Ser Val Thr Arg Ile Lys Lys Arg Ser Arg Ser Val Phe Tyr
        355                 360                 365
Arg Leu Thr Ile Leu Ile Leu Val Phe Ala Val Ser Trp Met Pro Leu
    370                 375                 380
His Leu Phe His Val Val Thr Asp Phe Asn Asp Asn Leu Ile Ser Asn
385                 390                 395                 400
Arg His Phe Lys Leu Val Tyr Cys Ile Cys His Leu Leu Gly Met Met
                405                 410                 415
Ser Cys Cys Leu Asn Pro Ile Leu Tyr Gly Phe Leu Asn Asn Gly Ile
            420                 425                 430
Lys Ala Asp Leu Val Ser Leu Ile His Cys Leu His Met
        435                 440                 445
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

TAGGGAACCT GGCCTCCTCC          20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

TCAGAGGGCC ATGACTCAAC          20

NEUROPEPTIDE Y RECEPTOR Y5 AND NUCLEIC ACID SEQUENCES

This application is a continuation of U.S. application Ser. No. 08/838,399, filed Apr. 7, 1997, now U.S. Pat. No. 5,965,392, which claims the benefit of U.S. Provisional Application No. 60/014,969, filed Apr. 8, 1996.

BACKGROUND OF THE INVENTION

1. Field of the Invention

This invention relates to a novel neurotransmitter Neuropeptide Y receptor, its nucleic acid sequence, and compounds, compositions, and methods for their use.

2. Summary of the Related Art

Neuropeptide Y (NPY) is a 36-amino acid peptide neurotransmitter that is located throughout the central and peripheral nervous systems. Tatemoto, *Proc. Natl. Acad Sci. USA* 79, 5485 (1982); Hazlewood, *Proc. Soc. Exp. Biol. Med.* 202, 44 (1993). It affects a broad range of phenomena, including blood pressure regulation, memory, anxiolysis/sedation, food and water appetite, vascular and other smooth muscle activity, intestinal electrolyte secretion, and urinary sodium excretion. E.g., Colmers and Wahlestedt, *The Biology of Neuropeptide Y and Related Peptides* (Humana Press, Totowa, N.J., 1993); Kalra et al., *Phys. & Behavior* 50, 5 (1991).

Peptide YY (PYY) is also a 36 amino acid peptide and has significant sequence homology (70%) to NPY. Tatemoto et al., *Nature* 296, 659 (1982). Its anatomical distribution is similar to that of NPY, although it is located mainly in the endocrine cells of the lower gastrointestinal tract. Bottcher et al., *Regul. Pept.* 8, 261 (1984). Like NPY, PYY stimulates feeding in rats. Morley et al., *Brain Res.* 341, 200 (1985). Along with the pancreatic polypeptide (PP), NPY and PYY have a common tertiary structure, characterized by the so-called PP-fold. Glover, *Eur. J. Biochem.* 142, 379 (1985). Both NPY and PYY show about a 50% sequence homology with PP.

Because of their structural similarities, NPY and PYY have a number of common receptors. At least four receptor subtypes, Y1, Y2, Y3, and Y4/PP, have been identified. The affinity for NPY, PYY, and various fragments thereof varies among the subtypes. See, e.g., Bard et al. (WO 95/17906) and references cited therein. For example, Y1 and Y2 subtypes have high affinity for NPY and PYY. Whereas Y1 has high affinity for (Leu$^{31}$Pro$^{34}$)NPY ((LP)NPY) and low affinity for (13-36)NPY, Y2 behaves oppositely. Y3 has high affinity for NPY but low affinity for PYY. Y4/PP has a high affinity for PP but relatively low affinity for NPY.

Wahlestedt (WO 93/24515) and Larhammar et al. (*J Biol. Chem.* 267, 10935 (1992)) describe the cloning and identification of the human Y1-type NPY/PYY receptor isolated from human fetal brain tissue. Selbie et al. (WO 93/09227) disclosed the full length cDNA sequence of the Y1 receptor from human hippocampus. Eva et al. (*FEBS Lett.* 271, 81 (1990)) cloned the NPY Y1 receptor from rat forebrain. Eva et al. (*FEBS Lett.* 314, 285 (1992)) cloned the NPY Y1 receptor from murine genomic DNA.

The Y2-type receptor has also been cloned. Gerald et al. (WO 95/21245) disclosed the cDNA sequence of human hippocampal Y2 and two rat Y2 clones. Rose et al. (*J. Biol. Chem.* 270, 22661 (1995)) disclosed the cDNA sequence of the Y2 receptor from a human neuroblastoma cell line.

Bard et al. (supra) and Lundell et al. (*J. Biol. Chem.* 270, 29123 (1995)) described cloning the cDNA sequence of the Y4/PP receptor from both rat spleen and human placenta.

To date, the Y3 receptor has not been cloned.

Because of the important role of NPY and PYY in a number of physiological processes., such as feeding, there is a strong need to further develop materials and methods for investigating the mechanistic behavior of these compounds and for treating diseased and other abnormal states associated with the physiological processes in which NPY and PYY act. Specifically, the NPY analogs/fragments that induce feeding, such as (LP)(3-36)NPY, do not bind to the previously identified NPY/PYY receptors with affinities consistent with the feeding response. Accordingly, there is a need and desire to identify the NPY/PYY receptor that is responsible for the feeding response. Antagonists to such a receptor could be used to treat obesity and diabetes by reducing appetite and food consumption.

SUMMARY OF THE INVENTION

The present invention provides, inter alia, novel NPY/PYY receptor proteins. Also provided are the nucleic acid sequences encoding these novel receptor proteins, as well is compounds and methods for using these proteins and their nucleic acid sequences.

The present invention provides novel proteins, nucleic acids, and methods useful for developing and identifying compounds for the treatment of such diseases and disorders as obesity. Identified and disclosed herein is the protein sequence for a novel receptor for the neurotransmitters Neuropeptide Y (NPY) and Peptide YY (PYY) and the nucleic acid sequence encoding this receptor, which we call the NPY Y5 (or simply "Y5") receptor. The importance of this discovery is manifested in the effects of NPY, which include blood pressure regulation, memory enhancement, anxiolysis/sedation, and increased food intake. Thus, this receptor protein is useful for screening for NPY/PYY agonist and antagonist activity for controlling these conditions.

In one aspect of the present invention, we provide isolated nucleic acid sequences for a novel NPY and PYY receptor, the Y5 receptor. In particular, we provide the cDNA sequences encoding for the rat and human receptors and isoforms thereof. These nucleic acid sequences have a variety of uses. For example, they are useful for making vectors and for transforming cells, both of which are ultimately useful for production of the Y5 receptor protein. They are also useful as scientific research tools for developing nucleic acid probes for determining receptor expression levels, e.g., to identify diseased or otherwise abnormal states. They are useful for developing analytical tools such as antisense oligonucleotides for selectively inhibiting expression of the receptor gene to determine physiological responses.

In another aspect of the present invention, we provide a homogenous composition comprising the receptor Y5 protein. The protein is useful for screening drugs for agonist and antagonist activity, and, therefore, for screening for drugs useful in regulating physiological responses associated with the Y5 receptor. Specifically, antagonists to the Y5 receptor could be used to treat obesity and diabetes by reducing appetite and food consumption, whereas agonists could be used for the treatment of anorexic conditions. The proteins are also useful for developing antibodies for detection of the protein.

Flowing from the foregoing are a number of other aspects of the invention, including (a) vectors, such as plasmids, comprising the receptor Y5 nucleic acid sequence that may further comprise additional regulatory elements, e.g., promoters, (b) transformed cells that express the Y5 receptor, (c) nucleic acid probes, (d) antisense oligonucleotides, (e) agonists, (f) antagonists, and (g) transgenic mammals. Further aspects of the invention comprise methods for making and using the foregoing compounds and compositions.

The foregoing merely summarizes certain aspects of the present invention and is not intended, nor should it be construed, to limit the invention in any manner. All patents and other publications recited herein are hereby incorporated by reference in their entirety.

DETAILED DESCRIPTION OF THE PREFERRED EMBODIMENTS

Figure 1:
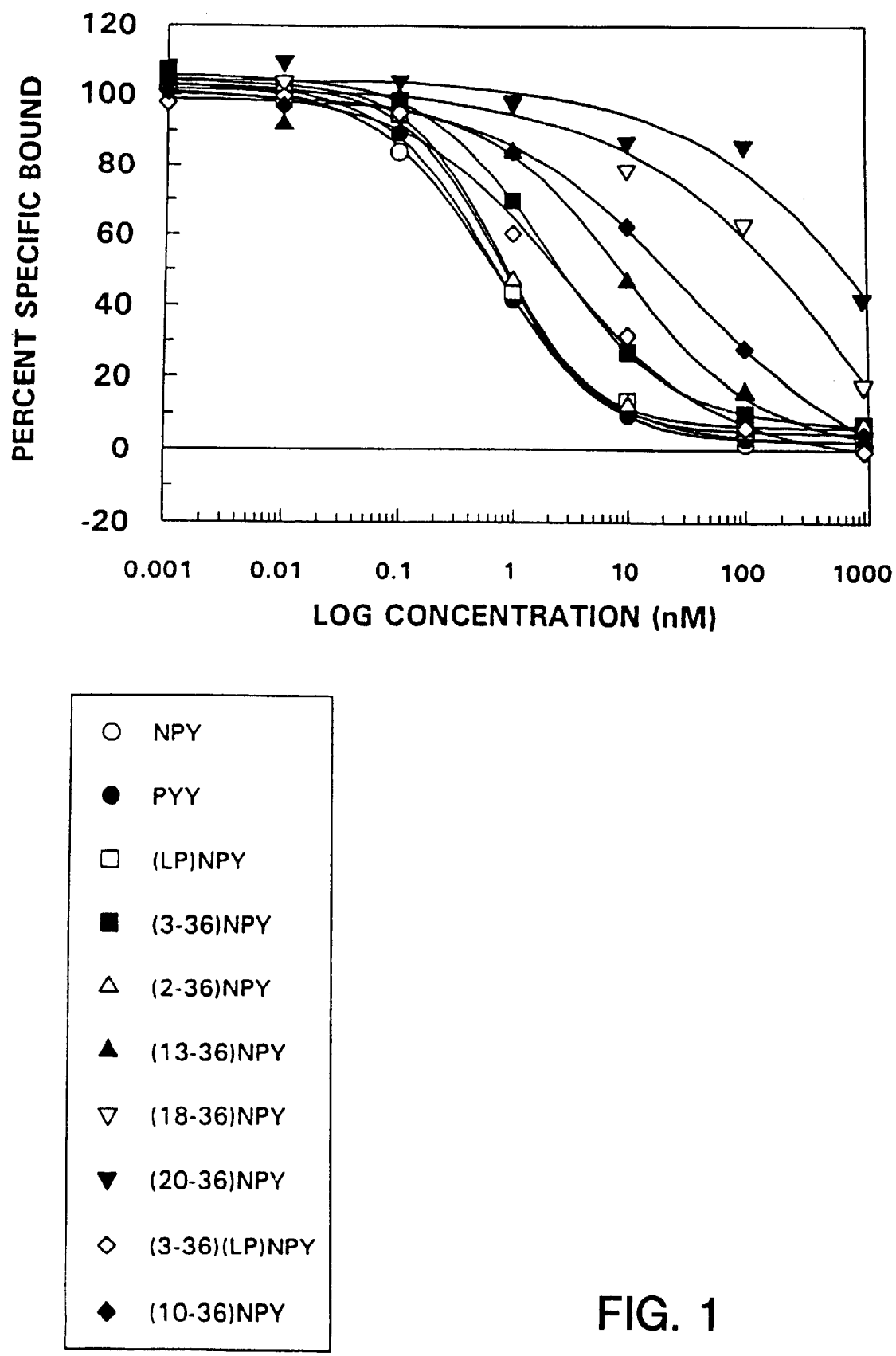
FIG. 1 displays the competition curves of various peptides for [$^{125}$I]PYY to Y5 receptor membranes transiently expressed in COS-7 cells.

The present invention comprises, in part, a novel NPY/PYY receptor protein, the Y5 receptor. Particularly preferred embodiments of the Y5 receptor are those having an amino acid sequence substantially the same as SEQ ID NOs 2, 4, or 6. As used herein, reference to the Y5 receptor is meant as a reference to any protein having an amino acid sequence substantially the same as SEQ ID NOs 2, 4, or 6. The present invention also comprises the nucleic acid sequence encoding the Y5 protein, which nucleic acid sequences is substantially the same as SEQ ID NOs 1, 3, or 5. Receptors SEQ ID NOs 2 and SEQ ID NO 4 are rat Y5 receptors and appear to be allelic variations, with SEQ ID NO 4 the most commonly occurring and, therefore, the preferred embodiment of the rat Y5 receptor of this invention. SEQ ID NO 6 is the human Y5 receptor and its preferred embodiment.

As used herein, a protein "having an amino acid sequence substantially the same as SEQ ID NO x" (where "x" is the number of one of the protein sequences recited in the Sequence Listing) means a protein whose amino acid sequence is the same as SEQ ID NO x or differs; only in a way such that IC$_{50}$[(3-36)NPY], IC$_{50}$[(Leu$^{31}$Pro$^{34}$)NPY], and IC$_{50}$[(Leu$^{31}$PRO$^{34}$)(3-36)NPY] as determined according to the method detailed in Example 4, infra, are less than or equal to 30 nM. The NPY fragments (3-36)NPY, (Leu$^{31}$Pro$^{34}$)NPY and (Leu$^{31}$Pro$^{34}$)(3-36)NPY induce a feeding response. Those skilled in the art will appreciate that conservative substitutions of amino acids can be made without significantly diminishing the protein's affinity for NPY, PYY, and fragments and analogs thereof. Other substitutions may be made that increase the protein's affinity for these compounds. Making and identifying such proteins is a routine matter given the teachings herein, and can be accomplished, for example, by altering the nucleic acid sequence encoding the protein (as disclosed herein), inserting it into a vector, transforming a cell, expressing the nucleic acid sequence, and measuring the binding affinity of the resulting protein, all as taught herein.

As used herein the term "a molecule having a nucleotide sequence substantially the same as SEQ ID NO y" (wherein "y" is the number of one of the protein-encoding nucleotide sequences listed in the Sequence Listing) means a nucleic acid encoding a protein "having an amino acid sequence substantially the same as SEQ ID NO y+1" (wherein "y+1" is the number of the amino acid sequence for which nucleotide sequence "y" codes) as defined above. This definition is intended to encompass natural allelic variations in the Y5 sequence. Cloned nucleic acid provided by the present invention may encode Y5 protein of any species of origin, including (but not limited to), for example, mouse, rat, rabbit, cat, dog, primate, and human. Preferably the nucleic acid provided by the invention encodes Y5 receptors of mammalian, and most preferably, rat or human origin.

The invention also includes nucleotide sequences encoding chimeric proteins comprised of parts of the Y5 receptor and parts of other related seven-transmembrane receptors.

The 6B clone (SEQ ID NO 1) (see Example 2, infra) has a 2.4 kb cDNA insert with a open reading frame from nucleotide 248 to 1582 that encodes a 445 amino acid protein (SEQ ID NO 2). Hydrophobicity plot analysis using PEPPLOT of GCG shows that the Y5 receptor has seven transmembrane-like domains, indicating it might be a G-protein-coupled receptor. Unlike other known subtypes of NPY receptor family, the third intracellular loop of the Y5 receptor is unusually long. Another novel feature of the Y5 peptide sequence is that it has a much shorter C-terminal tail sequence than other known members of the NPY receptor family. It is also important to note that the Y5 sequence shows only 30–33% amino acid sequence identity to other NPY receptors.

Nucleic acid hybridization probes provided by the invention are DNAs consisting essentially of the nucleotide sequences complementary to any sequence depicted in SEQ ID Nos 1, 3, and 5 that is effective in nucleic acid hybridization. Nucleic acid probes are useful for detecting Y5 gene expression in cells and tissues using techniques well-known in the art, including, but not limited to. Northern blot hybridization, in situ hybridization, and Southern hybridization to reverse transcriptase—polymerase chain reaction product DNAs. The probes provided by the present invention, including oligonucleotide probes derived therefrom, are also useful for Southern hybridization of mammalian, preferably human, genomic DNA for screening for restriction fragment length polymorphism (RFLP) associated with certain genetic disorders. As used herein, the term complementary means a nucleic acid having a sequence that is sufficiently complementary in the Watson-Crick sense to a target nucleic acid to bind to the target under physiological conditions or experimental conditions those skilled in the art routinely use when employing probes.

Receptor Y5 binds various fragments and analogs of NPY and PYY with affinities different from that of the known receptors. The rank order of binding affinity of receptor Y5 was found to be:

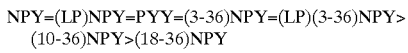

Table 1, infra, presents a more detailed affinity profile of the Y5 receptor for NPY, PYY, and various fragments thereof. As used herein, a protein having substantially the same affinity profile as the Y5 receptor means a protein in which the IC$_{50}$ of each of the peptides listed in Table 1, infra, is no more than an order of magnitude greater than those listed in Table 1 for each of the respective peptides as measured according to the methods described in Example 4. Importantly, the NPY analogs/fragments that induce feeding, such as (LP)(3-36)NPY, do not bind to the previously identified NPY/PYY receptors with affinities consistent with the feeding response.

The production of proteins such as receptor Y5 from cloned genes by genetic: engineering means is well known in this art. The discussion which follows is accordingly intended as an overview of this field, and is not intended to reflect the full state of the art.

DNA which encodes receptor Y5 may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the Y5 gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, the Y5 gene sequence may be obtained by use of the polymerase chain reaction (PCR.) procedure, with the PCR oligonucleotide primers being produced from the Y5 gene sequence provided herein. See U.S. Pat. No. 4,683,195 to Mullis et al. and U.S. Pat. No. 4,683,202 to Mullis.

Receptor Y5 may be synthesized in host cells transformed with a recombinant expression construct comprising a nucleic acid encoding the receptor Y5. Such a recombinant expression construct can also be comprised of a vector that is a replicable DNA construct. Vectors are used herein either to amplify DNA encoding Y5 and/or to express DNA which encodes Y5. For the purposes of this invention, a recombinant expression construct is a replicable DNA construct in which a DNA sequence encoding Y5 is operably linked to suitable control sequences capable of effecting the expression of Y5 in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., *Molecular Cloning: A Laboratory Manual* (2nd Edition, Cold Spring Harbor Press, New York, 1989).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. The vectors may be self-replicating. Suitable vectors for the purposes of the present invention include pBluescript, pcDNA3, and, for insect cells, baculovirus. A preferred vector is the plasmid pcDNA3 (Invitrogen).

Construction of suitable vectors containing the desired coding and control sequences employs standard ligation and restriction techniques that are well understood in the art. Isolated plasmids, DNA sequences, or synthesized oligonucleotides are cleaved, tailored, and relegated in the form desired.

Site-specific DNA cleavage is performed by treating with the suitable restriction enzyme (or enzymes) under conditions that are generally understood in the art, and the particulars of which are specified by the manufacturer of these commercially available restriction enzymes. See, e.g., *New England Biolabs, Product Catalog*. In general, about 1 $\mu$g of plasmid or DNA sequence is cleaved by one unit of enzyme in about 20 $\mu$l of buffer solution. Often excess of restriction enzyme is used to ensure complete digestion of the DNA substrate. Incubation times of about one hour to two hours at about 37° C. are workable, although variations are tolerable. After each incubation, protein is removed by extraction with phenol/chloroform, and may be followed by ether extraction. The nucleic acid may be recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65, 499–560 (1980).

Transformed host cells are cells which have been transformed or transfected with recombinant expression constructs made using recombinant DNA techniques and comprising mammalian Y5-encoding sequences. Preferred host cells for transient transfection are COS-7 cells. Transformed host cells may ordinarily express Y5, but host cells transformed for purposes of cloning or amplifying nucleic acid hybridization probe DNA need not express the receptor. When expressed, the mammalian Y5 protein will typically be located in the host cell membrane. See, Sambrook et al., ibid.

Cultures of cells derived from multicellular organisms are desirable hosts for recombinant Y5 protein synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture* (Academic Press, Kruse & Patterson, Eds., 1973). Examples of useful host cell lines are bacteria cells, insect cells, yeast cells, human 293 cells, VERO and HeLa cells, LMTK cells, and WI138, BHK, COS-7, CV, and MDCK cell lines. Human 293 cells are preferred.

The invention provides homogeneous compositions of mammalian Y5 produced by transformed eukaryotic cells as provided herein. Such homogeneous compositions are intended to be comprised of mammalian Y5 protein that comprises at least 90% of the protein in such homogenous composition. The invention also provides membrane preparation from cells expressing Y5 as the result of transformation with a recombinant expression construct, as described here.

Mammalian Y5 protein made from cloned genes in accordance with the present invention may be used for screening compounds for Y5 agonist or antagonist activity, or for determining the amount of a Y5 agonist or antagonist drug in a solution (e.g., blood plasma or serum). For example, host cells may be transformed with a recombinant expression construct of the present invention, Y5 protein expressed in those host cells, the cells lysed, and the membranes from those cells used to screen compounds for Y5 binding activity. Competitive binding assays in which such procedures may be carried out are well known in the art. By selection of host cells which do not ordinarily express Y5, pure or crude preparations of membranes containing Y5 can be obtained. Further, Y5 agonists and antagonists can be identified by transforming host cells with a recombinant expression construct as provided by the present invention. Membranes obtained from such cells (and membranes of intact cells) can be used in binding studies wherein the drug dissociation activity is monitored.

It is known that the neurotransmitter NPY is a regulator of appetite. As shown herein, the various NPY analogs/fragments that induce feeding, such as (LP)(3-36)NPY, bind with a high affinity to the Y5 receptor. Conversely, the NPY analogs/fragments that bind to the Y5 receptor with a lower affinity, such as (20-36)NPY, do not elicit feeding. It is therefore evident that by contacting the Y5 receptor with agonists and antagonists, feeding can be modulated. Accordingly, antagonists to the Y5 receptor, identified by the methods described herein, can be used to reduce appetite and hence treat obesity, diabetes and hyperlipidemia, and, conversely, agonists to the Y5 receptor can be used to treat conditions such as anorexia.

This invention provides a pharmaceutical composition comprising an effective amount of a agonist or antagonist drug identified by the method described herein and a pharmaceutically acceptable carrier. Such drugs and carrier can be administered by various routes, for example oral, subcutaneous, intramuscular, intravenous or intracerebral. The preferred route of administration would be oral at daily doses of about 0.01–100 mg/kg.

This invention provides a method of treating obesity, diabetes or hyperlipidemia, wherein the abnormality is improved by reducing the activity of Y5 receptor or blocking the binding of ligands to a Y5 receptor, which method comprises administering an effective amount of the antagonist-containing pharmaceutical composition described above to suppress the subject's appetite. Similarly, the invention also provides methods for treating diseases and conditions resulting from underfeeding and/or a loss of appetite, which method comprises administering an effective amount of an agonist-containing pharmaceutical composition described above to stimulate the subject's appetite.

The recombinant expression constructs of the present invention are useful in molecular biology to transform cells which do not ordinarily express Y5 to thereafter express this receptor. Such cells are useful as intermediates for making cell membrane preparations useful for receptor binding assays, which are in turn useful for drug screening. Drugs identified from such receptor assays can be used for the treatment of obesity, diabetes or anorexia.

The recombinant expression constructs of the present invention are also useful in gene therapy. Cloned genes of the present invention, or fragments thereof, may also be used in gene therapy carried out by homologous recombination or site-directed mutagenesis. See generally Thomas & Capecchi, *Cell* 51, 503–512 (1987); Bertling, *Bioscience Reports* 7, 107–112 (1987); Smithies et al., *Nature* 317, 230–234 (1985).

Oligonucleotides of the present invention are useful as diagnostic tools for probing Y5 gene expression in tissues. For example, tissues are probed in situ with oligonucleotide probes carrying detectable groups by conventional autoradiographic techniques, as explained in greater detail in the Examples below, to investigate native expression of this receptor or pathological conditions relating thereto. Further, chromosomes can be probed to investigate the presence or absence of the Y5 gene, and potential pathological conditions related thereto, as also illustrated by the Examples below. Probes according to the invention should generally be at least about 15 nucleotides in length to prevent binding to random sequences, but, under the appropriate circumstances may be smaller.

The invention also provides antibodies that are immunologically reactive to a mammalian Y5, preferably rat or human Y5. The antibodies provided by the invention are raised in animals by inoculation with cells that express a mammalian Y5 or epitopes thereof, using methods well known in the art. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses a mammalian Y5, or any cell or cell line that expresses a mammalian Y5 or any epitope thereof as a result of molecular or genetic engineering, or that has been treated to increase the expression of a mammalian Y5 by physical, biochemical or genetic means. Preferred cells are human cells, most preferably HEK 293 and BHK cells that have been transformed with a recombinant expression construct comprising a nucleic acid encoding a mammalian Y5, preferably a rat or human Y5, and that express the mammalian Y5 gene product.

The present invention provides monoclonal antibodies that are immunologically reactive with an epitope of mammalian Y5 or fragment thereof and that is present on the surface of mammalian cells, preferably human or mouse cells. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with cells expressing the Y5 receptor, preferably rat or human cells, as described above. The myeloma cell lines used in the invention include lines derived from myelomas of mice, rats, hamsters, primates and humans. Preferred myeloma cell lines are from mouse. The animals from whom spleens are obtained after immunization are rats, mice and hamsters, preferably mice, most preferably Balb/c mice. Spleen cells and, myeloma cells are fused using a number of methods well known in the art, including but- not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a mammalian Y5.

The present invention encompasses fragments of the antibody that are immunologically reactive with an epitope of a mammalian Y5. Such fragments are produced by any number of methods, including but not limited to proteolytic cleavage, chemical synthesis or preparation of such fragments by means of genetic engineering technology. The present invention also encompasses single-chain antibodies that are immunologically reactive with an epitope of a mammalian Y5 made by methods known to those of skill in the art.

The present invention also encompasses an epitope of a mammalian Y5 that is comprised of sequences and/or a conformation of sequences present in the mammalian Y5 molecule. This epitope may be naturally occurring, or may be the result of proteolytic cleavage of the mammalian Y5 molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an epitope that is a mammalian Y5. The chimeric antibodies embodied in the present invention include those that are derived from naturally occurring antibodies as well as chimeric antibodies made by means of genetic engineering technology well known to those of skill in the art.

Also provided by the present invention are non-human transgenic animals grown from germ cells transformed with the Y5 nucleic acid sequence according to the invention and that express the Y5 receptor according to the invention and offspring and descendants thereof. Also provided are transgenic non-human mammals comprising a homologous recombination knockout of the native Y5 receptor, as well as transgenic non-human mammals grown from germ cells transformed with nucleic acid antisense to the Y5 nucleic acid of the invention and offspring and descendants thereof. Further included as part of the present invention are transgenic animals which the native Y5 receptor has been replaced with the human homolog. Of course, offspring and descendants of all of the foregoing transgenic animals are also encompassed by the invention.

Transgenic animals according to the invention can be made using well known techniques with the nucleic acids disclosed herein. E.g., Leder et al., U.S. Pat. Nos. 4,736,866 and 5,175,383; Hogan et al., *Manipulating the Mouse Embryo, A Laboratory Manual* (Cold Spring Harbor Laboratory (1986)); Capecchi, *Science* 244, 1288 (1989); Zimmer and Gruss, *Nature* 338, 150 (1989); Kuhn et al., *Science* 269, 1427 (1995); Katsuki et al., *Science* 241, 593 (1988); Hasty et al., *Nature* 350, 243 (1991); Stacey et al., *Mol. Cell Biol.* 14, 1009 (1994); Hanks et al., *Science* 269, 679 (1995); and Marx, *Science* 269, 636 (1995). Such transgenic animals are useful for screening for and determining the physiological effects of Y5 receptor agonists and antagonist. Consequently, such transgenic animals are useful for developing drugs to regulate physiological activities in which NPY and/or PYY participate.

The following Examples are provided for illustrative purposes only and are not intended, nor should they be construed, as limiting the invention in any manner.

EXAMPLES

Example 1

Isolation and Sequencing of Rat Y5 Receptor
Isolation of Rat Hypothalamus mRNA and Construction of cDNA Library Expression cloning strategy was used to clone novel NPY receptor in rat hypothalamus cDNA library. RNA was obtained from 9 frozen rat hypothalami weighing a total of 0.87 grams. Poly(A) RNA was isolated directly from the tissue using the Promega PolyATtract System 1000 kit (Promega, Madison, Wis.). The hypothalami were homogenized in 4 mL of 4M guanidine thiocyanate-25 mM sodium citrate, pH 7.1–2% B-mercaptoethanol using a Polytron at full-speed for approximately 1 minute. To the homogenized tissue 8 mL of 4M guanidine thiocyanate-25 mM sodium citrate, pH 7.1–1% B-mercaptoethanol which had been preheated to 70° C. was added. After mixing thoroughly, 870 pmol biotinylated oligo(dT) was added; the mixture was incubated at 70° C. for 5 minutes. The homogenate was subjected to centrifugation at 12000×g for 10 minutes at room temperature; the homogenate was transferred to a clean tube and 10.44 mL Streptavidin MAGNESPHERE® Paramagnetic Particles (SA-PMPs) which had been prepared as per the published protocol was added. (Promega Corp. published protocol TM 228; Promega Corporation, Madison, Wis.). The homogenate and SA-PMPs were incubated together for 2 minutes at room temperature after which the homogenate was decanted while the SA-PMP-biotinylated oligo(dT)-hypothalamic poly(A) RNA complex was retained in the tube by a magnetic stand. The complex was washed as per the protocol, after which the RNA was precipitated and resuspended in water. 25 micrograms of this poly(A) RNA was used by Invitrogen (Invitrogen Corporation, San Diego, Calif. to prepare a cDNA expression library. The protocols used by Invitrogen to prepare the cDNA library are essentially based upon the procedures of Okayama and Berg (*Molec. Cell. Biol.* 2, 161 (1982)) and Gubler and Hoffman (Gene 25, 263 (1983)) (Invitrogen Corporation publications 130813sa and 130928sa). An oligo (dT) anchor primer was used for reverse transcription, and the library was cloned unidirectionally into pcDNA3 vector which contains a CMV promoter for eukaryotic expression. The cDNA library had $5.3 \times 10^5$ primary recombinants with an average insert size of 2.59 kb.

Isolation of a Novel Y5 Receptor cDNA Clone

The rat hypothalamus cDNA library was plated on the LB/Ampicillin plates in pools of 1,000 independent colonies. The plates were incubated at 37° C. for about 20 hours and the bacteria from each plate were scraped in 4–5 ml LB/Ampicillin media. Two ml of the bacteria samples were used for plasmid preparation and one ml of each pool was stored at −80° C. in 15% glycerol.

COS-7 cells were grown in Dulbecco's Modified Eagle Medium (DMEM, GIBCO 11965-092), 10% fetal bovine serum (GIBCO 16000-028), and 1× antibiotic/antimycotic solution (GIBCO 15240-039) (Gaithersburg, Md.). Cells were trypsinized and split at 50 to 70% confluency.

DNA from 1300 pools was transfected into COS-7 cells for $[^{125}I]$PYY binding assays. Twenty four hours before transfection, cells were plated into flaskette chambers (Nunc, Inc. 177453, Naperville, Ill.) at $3 \times 10^5$ cells/flaskette (equivalent to $3 \times 10^4$ cells/cm$^2$). Two $\mu$g of plasmid DNA from each pool was transfected into the cells using 10 $\mu$l of Lipofectamine is (GIBCO 18324-012) according to the manufacture's protocol. Forty eight hours after transfection, the $[^{125}I]$PYY binding assay was performed in the flaskette chamber. The cells were treated with 2 ml total binding buffer: 10 mM HEPES, 5 mM KCl, 1.2 mM KH$_2$PO$_4$, 2.5 mM CaCl$_2$, 1.2 MM MgSO$_4$, 150 mM NaCl, 25 mM NaHCO$_3$, 10 mg/ml bovine serun albumin, 0.5 mg/ml bacitracin and 0.4 mg/ml soybean trypsin inhibitor at room temperature for 15 minutes. The cells were then incubated with 100 pM porcine $[^{125}I]$PYY (Amersham (Arlington Heights, Ill.), Specific Activity 4000 Ci/mmol) in the total binding buffer for 90 minutes at room temperature. After binding, the cells were washed three times with ice-cold total binding buffer without ligand and one time with cold phosphate buffered saline (PBS). Cells were fixed with 1% cold glutaraldehyde in PBS for 15 minutes, washed once with cold PBS/0.5 M Tris, pH 7.5 and incubated in PBS/0.5 M Tris, pH 7.5 for 15 minutes at 4° C. After washing one more time with cold PBS, the slides were dipped in 0.5% gelatin at 42° C. and dried under vacuum. The dried slides were dipped in 50% photographic emulsion (Kodak (Rochester, N.Y.) NTB2) at 42° C. and exposed in the darkbox for four days at 4° C. After four days of exposure, the darkbox was moved to room temperature for one hour and slides were developed in developer D-19 (Kodak) for three minutes at 15° C. and fixed in fixer (Kodak) for three minutes at 15° C., washed in water and air dried. Cells were stained with Diff-Quik stain set (Baxter, McGaw Park, Ill.) and air dried. Slides were dipped into xylenes and mounted with DPX mountant (Electron Microscopy Science, Fort Washington, Pa.). Positive cells were identified using dark field microscopy.

Twenty one positive pools were identified. Since the hypothalamus expresses different subtypes of NPY receptors including Y1 and Y2 receptors, we analyzed all the positive pools for Y1, Y2 and Y4/PP receptors by PCR. Of the 21 positive pools tested as described above, 12 pools contained Y1, Y4 pools contained Y2 and none contained Y4/PP. Five pools (Y217, Y555, Y589, Y861 and Y1139) were negative by PCR analysis. The pool Y217 was subdivided in 24 subpools of 200 colonies, then 50 colonies, and finally a single clone, the Y217.24.13.6B clone (6B), was isolated.

DNA and Peptide Sequences Analysis

Plasmid DNA was sequenced by Lark Technologies Inc. (Houston, Tex.) and Biotechnology Resource Laboratory of Yale University (New Haven, Conn.) using Sequenase Kit (US Biochemical, Cleveland, Ohio) or Applied Biosystems' automatic sequencer system (model 373A). The peptide sequence was deduced from the long open-reading-frame of the nucleotide sequence. DNA and peptide sequences were analyzed using the GCG program (Genetics Computer Group, Madison, Wis.). The results are embodied in SEQ ID NO 1 (the nucleic acid sequence) and SEQ ID NO 2 (the amino acid sequence).

Example 2

Localization of Rat Y5 Receptor in Brain and Other Tissues

Northern Blot

To study the expression level of the Y5 receptor in the rat brain and other tissues, we did Northern blot analysis using the 6B 2.4 kb probe. A rat multiple tissue Northern blot (Clontech Laboratories, Palo Alto, Calif.) was hybridized to the $^{32}$P-labeled rat 6B probe. The blot contains 2 $\mu$g of poly A$^+$ RNA per lane from rat heart, brain, spleen, lung, liver, skeletal muscle, kidney, and testis. Hybridization was carried out in 1× hybridization solution containing 6X SSC (0.9 M NaCl, 0.09 M Na Citrate, pH 7.0), 5X Denhardt's solution (0.1% polyvinylpyrrolidone, 0.1% ficoll type 400, 0.1% bovine serum albumin), 100 mg/ml sheared, and denatured salmon sperm DNA at 65° C. The filter was washed at 65° C. in 0.1X SSC, 0.1% SDS and exposed to Kodak XAR 5 film with two intensifying screens. A single 2.6 kb band was detected in the brain after overnight exposure of the blot. No bands were found from other tissues (heart, spleen, lung, liver, skeletal muscle, kidney and testis) in the Clontech multiple tissue Northern blot, even after six days of exposure.

We tested 6B expression in more rat tissues and different regions of brain. mRNA was isolated from rat whole brain, cortex, hypothalamus, hippocampus, olfactory bulb, spleen, stomach, kidney, small intestine, adrenal and pancreas using Fast Track Isolation Kilt (Invitrogen). Ten $\mu$g of mRNA from different brain regions and multiple tissues were run on a denaturing formaldehyde 1% agarose gel, transferred to a Nytran membrane (Schleicher and Schuell) and hybridized with $^{32}$P-labeled 6B 2.4 kb probe and washed at high stringency. After overnight hybridization, the filter was washed at high stringency and exposed to X-ray film with intensifying screens. The 6B receptor mRNA was detectable in the brain regions examined after one day exposure, but no signal was observed from other tissues, even after a week exposure with double intensifying screens.

Example 3

Isolation of Two Isoforms of the Rat Y5 Receptor

Plasmid DNA from pools Y555, Y589, and Y861 described in Example 1 were hybridized to the Y5 probe at high stringency. A single positive clone was isolated from the Y555 pool and sequenced as described in Example 1. Compared to the 6B DNA sequence, the Y555 sequence (SEQ ID NO 4 has a 123 bp insert sequence located at the 5'-untranslated region between nucleotides 239 and 240 of Y5 clone. The coding region of the clones Y555, Y589, and Y861 has the same sequence as clone 6B, except for one nucleotide substitution (C to T) at position 430 of the 6B clone. The nucleotide substitution changes the amino acid proline to leucine in the first transmembrane domain. The corresponding amino acid sequence is given by SEQ ID NO 4.

The different isoforms of the receptor could be the allelic variants of the same gene. To test this hypothesis, we analyzed genomic DNA from 16 rats. The genomic DNA from each animal was used as template for PCR analysis. A 314 bp DNA fragment that contains the site of the nucleotide variation was amplified and sequenced. Of the 16 DNA samples tested, 14 samples had a T at position 430 and 2 samples had a C. This result strongly suggests that the amino acid variation is an allelic variant.

Example 4

Pharmacological Characterization of the Novel Rat NPY Receptors

Transient Transfection

Monkey kidney cells (COS-7) were maintained in T-175 cm$^2$ flasks (NUNC) at 37° C. with 5% CO$_2$ in a humidified atmosphere. Cells were grown in Dulbecco's Modified Eagle Medium (DMEM) supplemented with 2 mM glutamine, 10% fetal bovine serum, 1 mM sodium pyruvate, and antibiotic/antimycotic. Cells at 70% confluency were transfected with Y5 DNA using the Lipofectamine method (GIBCO-BRL). 15 $\mu$g DNA and 90 $\mu$l Lipofectamine were added to each flask. Media was completely replaced 24 hours post transfection, and membranes were harvested 24 hours later.

Stable Expression of the Rat NPY Y5 receptor (clone Y86 1)

A strain of the human embryonic kidney cell line 293 adapted to grow in suspension (293S) was used for these experiments. Approximately 1×10$^6$ cells were seeded onto a 10-cm dish 24 hours prior to transfection. The rat NPY Y5 cDNA (Y861), subcloned in the eukaryotic expression vector pcDNA3 (Invitrogen, Carlsbad, Calif.) was first linearized with NotI and purified using a Wizard PCR Prep kit (Promega). In preparation for transfection, 15 $\mu$g of the linearized DNA were added to 500 $\mu$l of DMEM cell culture media, and 30 $\mu$l of Lipofectamine (Life Sciences) were added into a separate 500 $\mu$l aliquot of DMEM. These two solutions were mixed together and incubated for 20 minutes at room temperature and the resulting DNA/lipid complexes were then slowly added to the cells (which had been previously rinsed once with serum-free DMEM) and covered with a total volume of 10 ml. Cells were then transferred to a humidified 10% $CO_2$ incubator and left for 4 hours at 37° C., at which time the media was replaced with DMEM supplemented with 8% FBS. After 16 hours, cells were trypsinized and split at a 1:15 ratio into 10-cm dishes containing DMEM8% FBS in the presence of 700 µg/ml of G418 (selection media). When discrete colonies became apparent (after approximately 10 days), cells were pooled and carried through 2 additional passages in selection media. Cells were then trypsinized and diluted in preparation for cloning by limited dilution (CBLD), such that an average of one cell was seeded in each well of a 96-well microtiter culture plate, and was inspected periodically for the subsequent 2 to 3 weeks. After 21 days in culture under selection conditions, those wells containing single colonies were selected and transferred to 24-well culture plates following trypsinization. Each of these clones was propagated until sufficient quantities were available for testing [$^{125}$I]PYY binding activity, from which one particular clone designated E7 was selected on the basis of its high level of binding activity.

Stable Expression of the human NPY Y5 receptor 293 cells were plated onto a T75 flask one day prior to transfection such that they were 50–70% confluent when used for the experiment. The human NPY Y5 intronless genomic clone HG.PCR15, containing the full length open reading frame encoding the receptor, was first linearized with Not I and purified using a Wizard PCR Prep kit (Promega). For each transfection, 8 µg of linearized DNA were added to 1.25 ml of Optimem culture media (Life Sciences) and 37 µl of Transfectam (Promega) were added to 1.25 ml of Optimem. These two solutions were then mixed together and added to cells previously washed once with Optimem. After an incubation period of 5 hours, the DNA/Transfectam mixture was removed, cells were washed with PBS and fed with DMEM supplemented with 10% FBS. Cells were left intact for two days, and then switched to selection media (DMEM 10% FBS containing 350 µg/ml of G418) for 5–10 days followed by CBLD as described above. The individual clone 293.hy5.sb.8 was selected on the basis of its high level of [$^{125}$I]PYY binding activity, using the intact cell binding protocol from above.

Membrane Preparation

The media was removed from each flask of transfected cells, and the cells were washed twice with 20 ml ice-cold phosphate buffered saline. The cells were scraped from the flask in 5 ml of Tris buffer (20 mM Tris-HCl and 5 mM EDTA, pH 7.7), and then transferred to a centrifuge tube. Each flask was washed with an additional 5 ml of Tris buffer and combined in the centrifuge tube. The cells were polytroned for 2×10 seconds (12 mm probe, 7000–8000 rpm) and centrifuged 5 minutes (Centra 7R, International Equipment Co., Needham Heights, Mass.) at 800 rpm and 4° C. The supernatant was then transferred to a clean centrifuge tube and was centrifuged at 30,000×g for 30 minutes and 4° C. The supernatant was removed and the pellet was stored at −80° C. Protein concentration was measured using the Bio-Rad kit pursuant to the standard manufacturer's protocol (Biorad Laboratories, Hercules, Calif.) with bovine IgG as the standard.

[$^{125}$I]PYY Binding Assay for NPY Y5 Receptors

The binding assays were performed on GF/C Millipore (Bedford, Mass.) 96-well plates pretreated with 0.02% polyethylenimine (PEI) for at least 2 hours prior to use. The PEI was aspirated from the plates on a vacuum manifold immediately before the samples were added to the wells. All peptides, tissue and radioligand were diluted with binding buffer (25 mM Tris, 120 mM NaCl, 5 mM KCl, 1.2 mM $KH_2PO_4$, 2.5 mM $CaCl_2$, 1.2 mM $MgSO_4$, 0.1% BSA and 0.5 mg/ml bacitracin, pH 7.4). For competition assays, increasing concentrations of peptide were incubated with [$^{125}$I]PYY and tissue. In a final volume of 200 µl, samples consisted of: membrane protein (i.e., 2.5–15 or 10–30 µg membrane protein for rat Y5 or human Y5, respectively); 75–100 µM [$^{125}$I]PYY NEN-DuPont (Boston, Mass.); peptide dilution or binding buffer. Nonspecific binding was defined by 1 µPYY. NPY, PYY, (2-36)NPY, (10-36)NPY, (LP)(3-36)NPY and (32D-Trp)NPY were synthesized at Bayer Corp. (West Haven, Conn.). All other peptides were purchased from either Peninsula (Belmont, Calif.) or Bachem (Torrance, Calif.).

For saturation experiments, increasing concentrations of [$^{125}$I]PYY were incubated with membrane and 1 µPYY. After a 2 hour incubation at room temperature with constant mixing, the samples were aspirated on a vacuum manifold. The wells were washed with three 200 µl aliquots of ice-cold binding buffer. The individual wells were punched into 12×75 mm plastic tubes, and counted on a Wallac (Gaithersburg, Md.) gamma counter. Binding data were analyzed using the nonlinear regression curve-fitting program RS/1 (BBN Software Products Corp., Cambridge, Mass.).

Binding Assays for Rat Y2, Y1, and Y4PP1 Receptors

The binding buffer for rat Y2 binding was Krebs/Ringer bicarbonate (Sigma K-4002, S-8875), pH 7.4, containing 0.01% bovine serum albumin (BSA-Sigma A-2153) and 0.005% bacitracin. 0.85–1 µg of protein and 25 pM [$^{125}$I] PYY are added to each well. Nonspecific binding is defined by 1 µM NPY.

The binding buffer for rat Y1 and rat Y4/PP1 binding consisted of 137 mM NaCl, 5.4 mM KCl, 0.44 mM $KH_2PO_4$, 1.26 mM $CaCl_2$, 0.81 mM $MgSO_4$, 20 mM HEPES, 1 MN dithiothreitol (DTT), 0.1% bacitracin, 100 mg/l streptomycin sulfate, 1 mg/l aprotinin, 10 mg/ml soybean trypsin inhibitor and 0.3% BSA, pH 7.4. For rat Y1 binding, ~5–15 µg of protein and 50 pM [$^{125}$I]PYY were added to each well, and nonspecific binding was defined by 1 µM NPY. For the rat Y4/PP1 binding assay, ~1–2 µg of protein and 50 pM rat [$^{125}$I]PP (NEN DuPont, Boston, Mass.) were added to each well, and 1 µM rat PP was used to define nonspecific binding.

In Vitro Functional Assay—Measurement of Forskolin-Stimulated Adenylate Cyclase

Rat Y5

(Reference: Gordon et al., J. Neurochem. 55, 506, 1990) Suspension cells stably expressing the Y5 receptor (approximately 400,000 per sample) were resuspended in serum-free DMEM containing 10 mM HEPES (pH 7.4) and 1 mM isobutylmethylxanthine (IBMX). 1 µM forskolin was added to the cells. The assay was stopped by transferring the samples into a boiling water bath for 3 minutes. After a 3 minute centrifugation at 14,000×g, an aliquot of each sample was quantitated for cAMP levels by radioimmunoassay (NEN DuPont, Mass.).

Human Y5

Monolayer cells stably expressing the Y5 receptor were pre-rinsed with Wash buffer (pH 7.2: 137 mM NaCl, 2.7 mM KCl, 0.9 mM $CaCl_2$, 0.5 mM $MgCl_2$, 6.5 mM $Na_2HPO_4$, 1.5 mM $KH_2PO_4$). Cells were then incubated for 10 minutes at 37° C. in Assay buffer (pH 7.4: Wash buffer+10 mM HEPES, 10 mg/ml BSA, 0.5 mg/ml bacitracin, 0.4 mg/ml soybean trypsin inhibitor). After addition of fresh buffer and 100 μM IBMX, the cells were incubated for 10 minutes at 37° C. The reaction was started with the addition of peptide and 1–10 μM forskolin. After a 20 minute incubation at 37° C., the reaction was terminated by discarding the buffer and adding 65% ethanol to each well. The supernatant was then transferred to microfuge tubes and the extraction step was repeated once more. After evaporation of the ethanol from the samples, the amount of cAMP was assayed using by radioimmunoassay (MEN DuPont: Boston, Mass.).

In Vivo Pharmacology Procedures

Adult male Wistar rats were surgically implanted with a chronic intracerebral ventricular (ICV) cannula (Plastic Products, Roanoke, Virginia) using a stereotaxic instrument. Several days after the surgery, 1–6 nmoles of each peptide (or saline) was injected into the lateral ventricle of 4–12 rats in a volume of 5–10 μl. The quantity of rodent chow consumed in a 2 hour period was measured.

In Vitro and In Vivo Pharmacology Results

FIG. 1 presents the competition curves of various peptides for [$^{125}$I]PYY binding to Y5 receptor membranes transiently expressed in COS-7 cells. Each point is the average value of triplicate determinations from a representative experiment. $IC_{50}$ values corresponding to 50% inhibition of specific binding were determined using nonlinear regression analysis. $K_i$ values were calculated from the $IC_{50}$ values using the Cheng-Prusoff correction, such that $K_i=IC_{50}/(1\pm(L/K_d))$, where L is the radioligand concentration and $K_d$ is the dissociation constant. The results for transiently expressed Y5 clones are presented in Table 1, and Table 2 contains data for stably expressed Y5 clones.

TABLE 1

NPY Y5 BINDING AFFINITIES ($K_i$ ± SEM, nM)

| PEPTIDE | RAT Y555 Clone* | RAT 6B Clone | RAT Y861 Clone | HUMAN Clone |
|---|---|---|---|---|
| r/hNPY | 0.53 ± 0.06 | 0.49 ± 0.03 | 0.50 ± 0.06 | 0.73 ± 0.09 |
| rPYY | 1.1 (1.2, 0.95) | 0.48 ± 0.09 | 1.0 ± 0.13 | 1.3 ± 0.14 |
| h(LP)PYY | 2.5 ± 0.5 | 0.57 ± 0.01 | 1.8 ± 0.09 | 1.7 ± 0.3 |
| r/h(LP)NPY | 0.96 (1.0, 0.92) | 0.31 | 0.55 ± 0.11 | 0.97 ± 0.36 |
| p(LP)NPY | ND | 0.64 ± 0.07 | 0.47 | 0.88 ± 0.11 |
| r/h(2-36)NPY | 0.81 (0.61, 1) | 0.65 | 1.2 ± 0.07 | 1.2 ± 0.15 |
| p(3-36)NPY | 3.6 ± 0.4 | 1.9 ± 0.27 | 2.0 (1.8, 2.3) | 10.4 ± 2.0 |
| r/h(3-36)NPY | ND | 0.49 | 2.1 (2.7, 1.6) | 3.8 ± 0.48 |
| r(3-36)PYY | 6.2 ± 1.1 | 1.4 ± 0.10 | 4.2 ± 0.47 | 10 ± 3.4 |
| r/h(10-36)NPY | 35 | 4.9 (6.0, 3.8) | 34 ± 2.8 | 110 (110, 109) |
| p(13-36)NPY | 40 (38, 41) | 7.7 (7.9, 7.5) | 22 (25, 19) | 56 ± 7 |
| r(13-36)NPY | 73 | 11 ± 1.0 | 86 ± 19 | 77 (89, 65) |
| p(18-36)NPY | 303 | 194 ± 88 | 206 ± 61 | 618 ± 85 |
| r/h(20-36)NPY | 636 | 330 ± 31 | 587 | >1000 |
| r/h(22-36)NPY | >1000 | >1000 | >1000 | >1000 |
| r/h(26-36)NPY | >1000 | >1000 | >1000 | >1000 |
| (1-24)NPY | ND | >1000 | >1000 | >1000 |
| BIBP3226 | ND | >1000 | >1000 | >1000 |

TABLE 1-continued

NPY Y5 BINDING AFFINITIES ($K_i$ ± SEM, nM)

| PEPTIDE | RAT Y555 Clone* | RAT 6B Clone | RAT Y861 Clone | HUMAN Clone |
|---|---|---|---|---|
| hPP | ND | ND | 4.0 ± 0.29 | 11 (15, 6.2) |
| rPP | ND | 62 | 296 ± 47 | 436 (582, 290) |

*$IC_{50}$ values (nM)

TABLE 2

| | $K_i$ Values (nM; Average ± SEM) | |
|---|---|---|
| Peptide | 293.hY5.sb.8 | 293S.Y861.2 |
| rPYY | 1.3 ± 0.2 | 0.71 ± 0.1 |
| hPYY | 1.1 ± 0.2 | 1.06 ± 0.2 |
| (3-36)PYY | 4.5 ± 0.7 | 3.6 ± 0.4 |
| (13-36)PYY | 24 ± 2.9 | 29 ± 4 |
| h(LP)PYY | 1.3 ± 0.1 | 0.76 ± 0.1 |
| r/hNPY | 0.79 ± 0.1 | 0.86 ± 0.07 |
| p(LP)NPY | 1.2 ± 0.4 | 0.67 ± 0.04 |
| h/r(LP)NPY | 0.89 ± 0.1 | 0.67 ± 0.04 |
| (LP)(3-36)NPY | 3.1 ± 0.6 | 2.9 ± 0.9 |
| (2-36)NPY | 1.4 ± 0.03 | 0.83 ± 0.1 |
| h(3-36)NPY | 3.5 ± 0.4 | 1.4 ± 0.4 |
| (10-36)NPY | 14 ± 2.7 | 15 ± 4.7 |
| p(13-36)NPY | 8.7 ± 1.6 | 8.8 ± 2.0 |
| p(18-36)NPY | 144 ± 18 | 61 ± 13 |
| (20-36)NPY | 429 ± 133 | 108 ± 16 |
| (22-36)NPY | >900 | >930 |
| (26-36)NPY | >900 | >930 |
| (1-24)NPY | >900 | >930 |
| (32D-Trp)NPY | 7.3 ± 0.8 | 4.2 ± 1.0 |
| hPP | 3.7 ± 1.6 | 2.5 ± 0.5 |
| rPP | 286 ± 77 | 203 ± 44 |

$K_i$ values for various peptides for [$^{125}$I]PYY binding to the transiently expressed rat 6B, Y861 and Y555 receptor clones as well as the human Y5 receptor. The average standard error of the mean (SEM) represent values from at least three independent experiments. Two independent experiments are represented by the average, followed by the individual values in parentheses. Remaining values without SEM are from a single experiment. Peptide species in Table 1 (and Table 2, infra) are indicated with the following prefixes: r=rat, h=human, p=porcine, r/h=rat=human. ND=not determined.

The rank order of the affinities of the peptides tested is as follows:

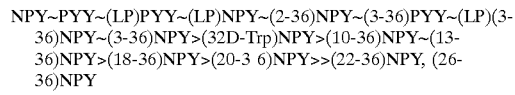
NPY~PYY~(LP)PYY~(LP)NPY~(2-36)NPY~(3-36)PYY~(LP)(3-36)NPY~(3-36)NPY>(32D-Trp)NPY>(10-36)NPY~(13-36)NPY>(18-36)NPY>(20-3 6)NPY>>(22-36)NPY, (26-36)NPY In Table 3, the pharmacological profile of the standard peptides is expanded for the other cloned NPY receptors to further illustrate the novel nature of the Y5 receptor pharmacology. In addition, the in vivo feeding response of some of these peptides is listed for comparison. The data shown are representative of the average of at least two independent experiments, as described in the methods. Feeding of rats injected (ICV) with saline was<3 g/2 hours.

Table 4 shows the $EC_{50}$ values for same standard peptides at the rat and human Y5 receptor.

C-terminal fragment (3-36)NPY binds preferentially to Y2 receptors, while (LP)NPY has lower affinity. Conversely, (LP)NPY has high affinity for the Y1 receptor, while (3-36)NPY and the C-terminal fragments are much weaker. When considering the rat Y4/PP1 receptor, rat PP has very high affinity as compared to NPY, PYY, (LP)NPY, and (13-36) NPY. In the in vivo feeding model, (LP)NPY, which has high affinity for Y1 and low affinity for Y2, and (3-36)NPY, which has a high affinity for Y2, but not Y1, all stimulate feeding in rats. Rat PP does not induce much feeding when administered to rats. This in vivo profile matches the in vitro pharmacological profile outlined in Table 2 for the Y5 receptor.

In addition, while (LP)(3-36)NPY (a custom peptide synthesized at Bayer) has weak affinity for Y1, Y2 and Y4/PP1, it stimulates feeding in rats. Importantly, (LP)(3-36)NPY has high affinity for the Y5 receptor (Table 2). These data are further evidence that the Y5 receptor is linked to feeding.

TABLE 3

| PEPTIDE | IC$_{50}$ VALUE (nM) | | | | |
| --- | --- | --- | --- | --- | --- |
| | Rat Y1 (clone) | Rat Y2 (clone) | Rat Y4/PP1 (clone) | Rat Y5 (Y861) | Feeding (g/2 h) |
| r/hNPY | 0.13 | 0.24 | >1000 | 0.45 | >5 |
| rPYY | 0.43 | 0.079 | 630 | 0.9 | >5 |
| h(Leu$^{31}$Pro$^{34}$)PYY | 0.57 | 116 | ND | 2.0 | >5 |
| p(Leu$^{31}$Pro$^{34}$)NPY | 0.15 | 150 | 4.3 | 0.63 | >5 |
| r/h(2-36)NPY | 47 | 0.50 | >1000 | 1.3 | >5 |
| p(3-36)NPY | 45 | 0.67 | >1000 | 2.2 | >5 |
| r/h(Leu$^{31}$Pro$^{34}$)(3-36)NPY | 44 | 154 | 20 | 3.4 | >5 |
| hPP | 40 | >1000 | 0.065 | 4.9 | >5 |
| (32DTrp)NPY | >1000 | 26 | ND | 7.0 | ND |
| r/h(10-36)NPY | 148 | 0.42 | >1000 | 34 | <3 |
| rPP | 843 | >1000 | 0.071 | 325 | <3 |
| p(18-36)NPY | 287 | 0.34 | 159 | 326 | <3 |
| (20-36)NPY | 435 | 0.64 | ND | 638 | <3 |
| (22-36)NPY | >1000 | 0.89 | ND | >1000 | <3 |
| (26-36)NPY | >1000 | 84 | ND | >1000 | <3 |
| (1-24)NPY | >1000 | >1000 | ND | >1000 | <3 |

The pharmacological profile for the 6B (and Y861 and Y555) receptor clones is distinct from Y1 receptors (where PYY~NPY~(LP)NPY>(3-36)NPY>(13-36)NPY~(18-36)NPY>(LP)(3-36)NPY), as well as Y2 receptors (where PYY~NPY~(13-36)NPY~(18-36)NPY~(3-36)NPY>>(LP)NPY~(LP)(3-36)NPY). The Y5 receptor is also different from the pancreatic polypeptide (PP) receptor (Y4/PP) since [$^{125}$I]pp (rat) does not bind to it.

Although the rank order of affinities is essentially the same when comparing 6B to Y861 and Y555, subtle differences do exist in the IC$_{50}$ values. It appears that Y861 and Y555 have slightly lower affinities (approximately 2- to 3-fold) for PYY and other PYY analogs, as compared to 6B. In addition, (10-36)NPY and (13-36) have 2- to 4-fold lower affinity for Y861 and Y555.

Nonlinear regression analysis of saturation data for the Y5 receptor yielded a K$_d$ value of 0.27 nM and a receptor density (B$_{max}$) of about 140 fmol/mg protein in these transiently transfected cells.

Figure 2A:
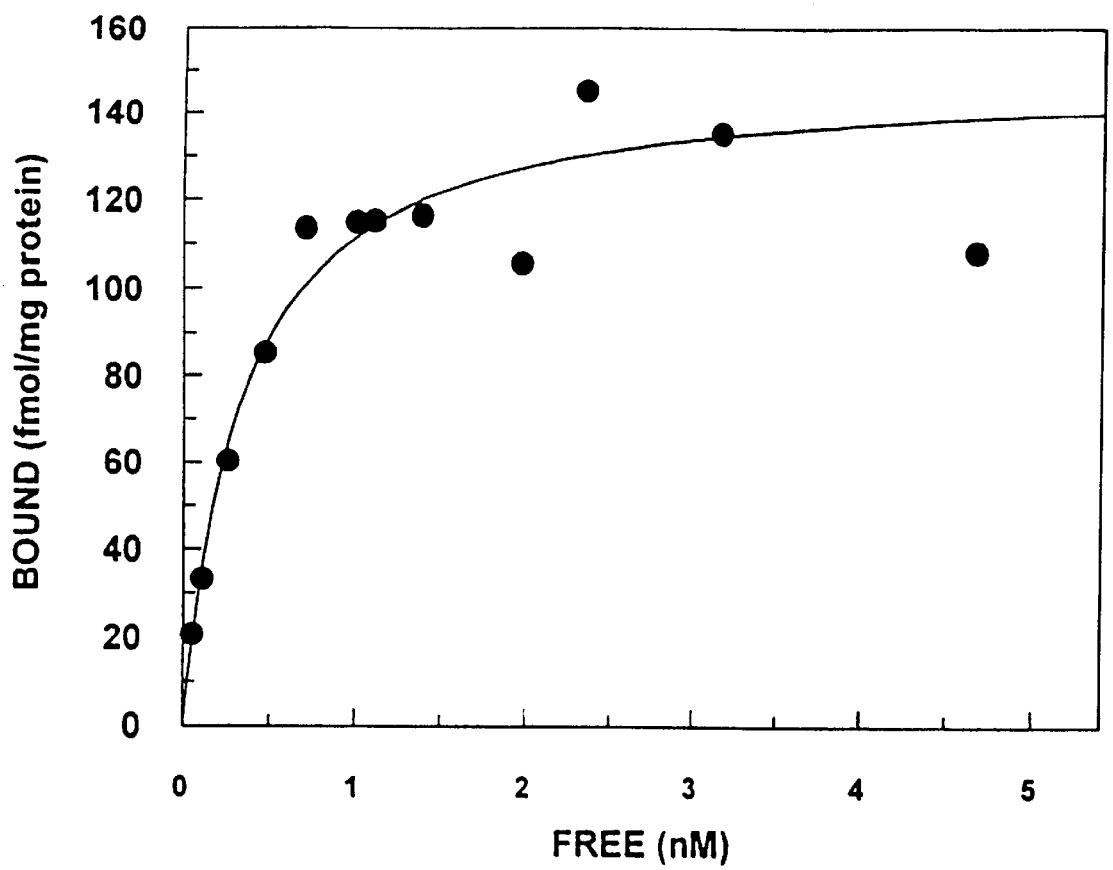
FIGS. 2A–2B display saturation curves for specific binding of [$^{125}$I]PYY to Y5 receptor membranes transiently expressed in COS-7 cells.
Figure 2B:
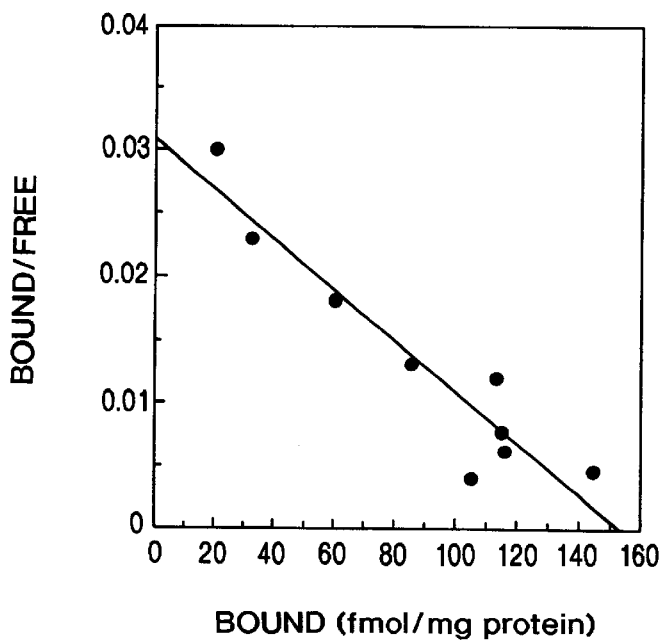

FIG. 2 presents the saturation curve for specific binding of [$^{125}$I]PYY to Y5 receptor membranes transiently expressed in COS-7 cells. Membranes were incubated with concentrations of [$^{125}$I]PYY ranging from 0.05 to 5 nM, in the presence or absence of 1 µM PYY. Each point represents the average value of triplicate determinations at each concentration tested. The inset in FIG. 2 shows the corresponding Rosenthal plot of the data.

TABLE 4

| | EC$_{50}$ Values, nM (n Value) | |
| --- | --- | --- |
| Peptide | 293S.Y861.2 | 293.hY5.sb.8 |
| r/hNPY | 6.3 ± 1.9 (3) | 0.3 (1) |
| rPYY | 6.5 (2) | ND |
| r/h(2-36)NPY | 21 (2) | ND |
| r/h(3-36)NPY | ND | 6 (1) |
| r/h(LeuPro)(3–36)NPY | 31 ± 39 (3) | 23 ± 11 (3) |
| (32D-Trp)NPY | 24 (1) | 33 (1) |
| hPP | 1 (1) | 5 (1) |
| rPP | 112 (1) | >1000 (1) |

Example 5

Isolation of Human Y5 Receptor

Isolation of Human Genomic Clone

Polymerase chain reaction (PCR) was used to amplify a 375 base pair (bp) coding region of the rat Y5 cDNA clone. The primers for the PCR were:

(+) 5'-TAGGGAACCTGGCCTCCTCC-3' (SEQ ID: NO 7) (nucleotides 486)-505), (−) 5'-TCAGAGGGCCATGACTCAAC-3' (SEQ ID NO: 8) (nucleotides 842)-861).

The PCR product was cloned into pCRII vector (Invitrogen) and sequenced. After confirmation by sequencing, the insert was purified from the low melting gel and labeled with digoxigenin-11-dUTP using the random primed method (Boehringer Mannheim, Ind.). The labeled probe was used to screen human genomic library.

1×10$^6$ independent recombinants were screened from the library. Filter hybridization was carried out in the hybridization buffer containing 6×SSC, 0.1% N-lauroylsarcosine, 0.02% sodium dodecyl sulfate (SDS), 3% blocking reagent (Boehringer Mannheim) and 30% formamide at 37° C. overnight. The filters were washed at 37° C. in 0.1×SSC, 0.1% SDS and the positive clones were identified by CSPD detection kit according to the manufacturer's protocol (Boehringer Mannheim).

Two positive clones (HG11A and HG19) were isolated from the library. The positive clones were subcloned into pBluescript vector (Stratagene). One clone, h11a, was analyzed by restriction mapping and plasmid Southern blot. Two EcoRV fragments, 2.4 kb and 0.4 kb, were hybridized by the rat Y5 probe. These two DNA fragments were subcloned and sequenced from both ends. DNA sequence analysis was performed using GCG program. The coding region of the human Y5 genomic clone was identified by DNA sequence analysis. This region was amplified by PCR using genomic clone h11A as template and subcloned into pcDNA3 expression vector (Invitrogen) for further studies. The h11A clone has the nucleic acid coding sequence given by SEQ ID NO 5 and the protein that it encodes has the amino acid sequence given by SEQ ID NO 6.

The human Y5 DNA coding region was used to search the sequence similarities in the gene bank. The Y5 coding sequence from nucleotide 821 to the stop codon at position 1338 is nearly identical, but in an opposite orientation, to part of the human NPY-Y1 gene (Ball et al, J. Biol. Chem. 270, 30102 (1995)). The identical sequence covered the 1C exon promoter, exon 1C, and part of the intron sequences of the NPY-Y1 receptor in an opposite orientation. Compared to the published nucleotide sequence, the Y5 coding region has a T insertion at position 1226 and a TG insertion at positions 1235 and 1236.

We claim:

1. An isolated nucleic acid cloned from a mammalian genomic library using a digoxigenin-labeled hybridization probe, the nucleic acid comprising a sequence that hybridizes to the probe under the following hybridization conditions: hybridization in buffer containing 6×SSC, 0.1% N-lauroylsarcosine, 0.02% sodium dodecyl sulfate, 3% blocking reagent, and 30% formamide at 37° C. and washing with 0.1×SSC and 0.1% sodium dodecyl sulfate at 37° C., wherein the probe is complementary to nucleotides 486–861 of SEQ ID NO: 1, and the nucleic acid encodes a protein whose amino acid sequence consists of 445 amino acids and whose IC50{(3-36)NPY}, IC50{(Leu31Pro34)NPY}, and IC50{(Leu3Pro34)(3-36)NPY} are less than or equal to 30 nM.

2. A vector comprising the nucleic acid according to claim 1.

3. A vector according to claim 2 further comprising regulatory elements operatively linked to the nucleic acid to enable expression of the nucleic acid in a host cell.

4. A vector according to claim 2 wherein the cell is a mammalian cell.

5. A vector according to claim 2 wherein the cell is a human 293 cell.

6. A vector according to claim 2 that is a plasmid.

7. The vector according to claim 2 wherein the vector is a plasmid.

8. The vector according to claim 6 wherein the plasmid is the pcDNA3 plasmid.

9. An isolated cell wherein the cell is transformed with the nucleic acid according to claim 1 and expresses the protein encoded by the nucleic acid.

10. A cell according to claim 9 that is a mammalian cell.

11. A cell according to claim 10 that is a human 293 cell.

12. An isolated nucleic acid probe comprising a nucleic acid complementary to the nucleic acid according to claim 1.

13. A method of producing a neuropeptide Y5 receptor comprising culturing a host cell transformed with the nucleic acid according to claim 1 under conditions that allow expression of the receptor and recovering the receptor.

14. The method according to claim 13 where the cell is a mammalian cell.

15. The method according to claim 13 where the cell is a human 293 cell.

* * * * *